US006924145B1

(12) United States Patent
Jorsboe et al.

(10) Patent No.: US 6,924,145 B1
(45) Date of Patent: Aug. 2, 2005

(54) SELECTION METHOD

(75) Inventors: Morten Jorsboe, Nykobing F (DK); Janne Brunstedt, Roskilde (DK); Kirsten Jorgensen, Guldborg (DK)

(73) Assignee: Danisco A/S, Copenhagen (DK)

( * ) Notice: Subject to any disclaimer, the term of this patent is extended or adjusted under 35 U.S.C. 154(b) by 0 days.

(21) Appl. No.: 09/762,629

(22) PCT Filed: Aug. 11, 1999

(86) PCT No.: PCT/IB99/01465

§ 371 (c)(1),
(2), (4) Date: May 14, 2001

(87) PCT Pub. No.: WO00/09705

PCT Pub. Date: Feb. 24, 2000

(30) Foreign Application Priority Data

Aug. 11, 1998 (GB) .............................. 9817465

(51) Int. Cl.[7] ........................ C12N 15/52; C12N 15/54; C12N 15/82
(52) U.S. Cl. ...................... 435/468; 435/419; 435/193; 435/425; 800/278
(58) Field of Search ................................ 435/425, 419, 435/468, 471; 800/278, 284, 208, 295, 298; 536/28.1, 23.2, 23.8, 23.7

(56) References Cited

U.S. PATENT DOCUMENTS 5,767,378 A * 6/1998 Bojsen et al. ............... 800/205

FOREIGN PATENT DOCUMENTS

| EP | 0 235 112 | 2/1987 |
|---|---|---|
| WO | WO 93/05163 | 3/1993 |
| WO | WO 94/20627 | 9/1994 |
| WO | WO 96/09374 | 3/1996 |
| WO | WO 96/31612 | 10/1996 |
| WO | WO 98/35047 | 8/1998 |
| WO | WO 98/54334 | 12/1998 |
| WO | WO 99/37786 | 7/1999 |

OTHER PUBLICATIONS

NCBI GI: 345849; Sep. 30, 1993.*
NCBI GI: 96872; Aug. 1990.*
NCBI GI: 153260 Apr. 26, 1993.*
NCBI GI: 1786973; Jan. 16, 1997.*
Pasco–Gaunt S. et al. Journal of Experimental Botany; vol. 52, No. 357; pp. 865–874.*
Mollet B et al. Journal of Bacteriology, Jul. 1991; vol. 173, No. 14; pp. 4464–4473.*
Dormann P. et al., The Plant Journal, Mar. 1998; vol. 13 No. 5; pp. 641–652.*
Schumperli et al., (Jan.) 1982, Proc. Natl. Acad. Sci. USA, 79:257261, "Efficient expression of Escherichia coli galactokinase gene in mammalian cells".
Asad Ahmed, 1984, Gene 28:37–43, "Plasmid vectors for positive galactose–resistance selection of cloned DNA in Escherichia coli".
Hess et al., 1984, Journal of Plant Physiology, 116:261–272 "Bacterial transferase activity expressed in Petunia grogenies" (Abstract Only).
Dormann et al., 1998, The Plant Journal, 13(5):641–652, "The role of UDP–glucose epimerase in carbohydrate metabolism of Arabidopsis".
Dormann et al., 1996, Archives of Biochemistry and Biophysics, 327:27–34, "Functional Expression of Uridine 5'–Diphospho–Glucose 4–Epimerase (EC 5.1.3.2) from Arabidopsis thaliana in Saccharomyces cerevisiae and Escherichia coli".
Daude et al., 1995, Biochem. Mol. Med, 56(1):1–3 "Molecular cloning, characterization, and mapping of a fullength cDNA . . . " (Medline cite only).
Maccratesi et al., Mol. Gent. Metab. 63(1):26–30, "Human UDP–galactose 4'–epimerase (GALE) gene and identification of five missense mutations in patients . . . " (Medine cite only).
Reichardt et al., (Sep. 2) 1997, EMBL GenBank/DDBJ databases, Accession No. 014376; GALE–Human, (Sequence).
Leslie et al., 1993, Genomics 14:474–480 "The human galactose—phosphate uridyltransferase gene".
Joersbo et al., 1997, Molecular Breeding, 4:111–117, "Analysis of mannose selection used for transformation of sugar beet".
Roberts et al., 1971, Plant Physiol, 48(1):36–45, Growth inhibition and metabolite pool levels in plant tissue fed D–glucosamine and D–galactose, 1971, pp. 3645.
Haldrup et al., 1998, Plant Molecular Biolog. 37:287–296, "The xylose isomerase gene from Thermoanaerobacterium thermosulfurogenes allows effective selection of transgenic plant cells using D–xylose as the selection agent".
Elisabeth Johansen, (Oct.) 1996, Proc. Natl. Acad. Sci. USA, 93:12400–12405, "Intron insertion facilitates amplification of cloned virus cDNA in Escherichia coli while biological activityis reestablished after transcription in vivo".
International Search Report for application PCT/IB99/01465.

* cited by examiner

Primary Examiner—David T. Fox
Assistant Examiner—Rusell Kallis
(74) Attorney, Agent, or Firm—Merchant & Gould P.C.

(57) ABSTRACT

A selection method for selecting from a population of cells one or more selectable genetically transformed cells is described. The population of cells comprises selectable genetically transformed cells and possible non-transformed cells. Each of the selectable genetically transformed cells comprises a first expressable nucleotide sequence encoding a first expression product; and optionally a second expressable nucleotide sequence encoding a second expression product and/or a third expressable nucleotide sequence encoding a third expression product. A component is utilisable by the selectable genetically transformed cells by action of the first expressable nucleotide sequence or the first expression product and optionally by action of the optional second expressable nucleotide sequence or the optional second expression product and/or by, action of the optional third expressable nucleotide sequence or the optional Third expression product. The component can be present in an amount that is toxic to the non-transformed cells.

17 Claims, 3 Drawing Sheets

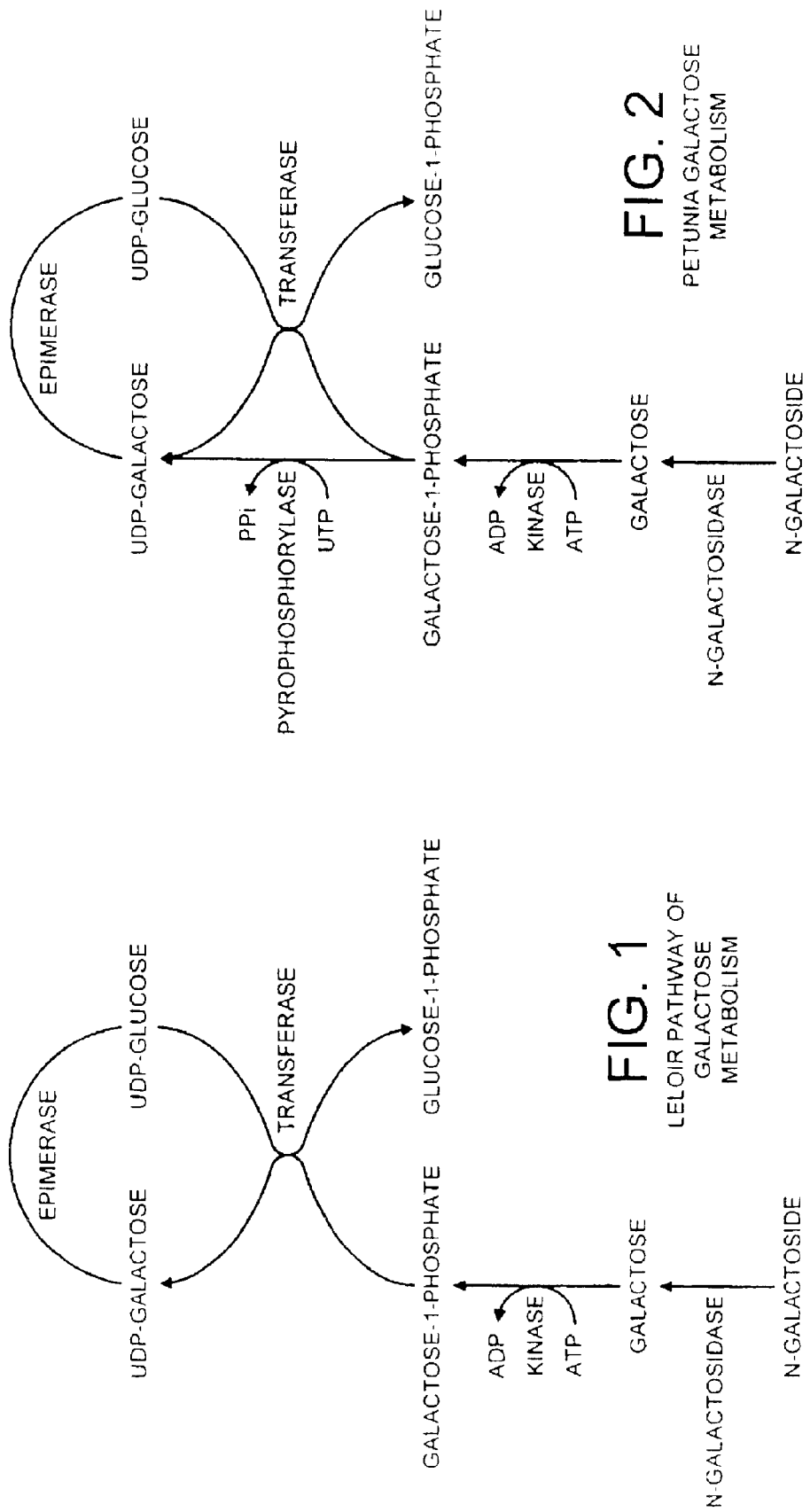

Figure 4:
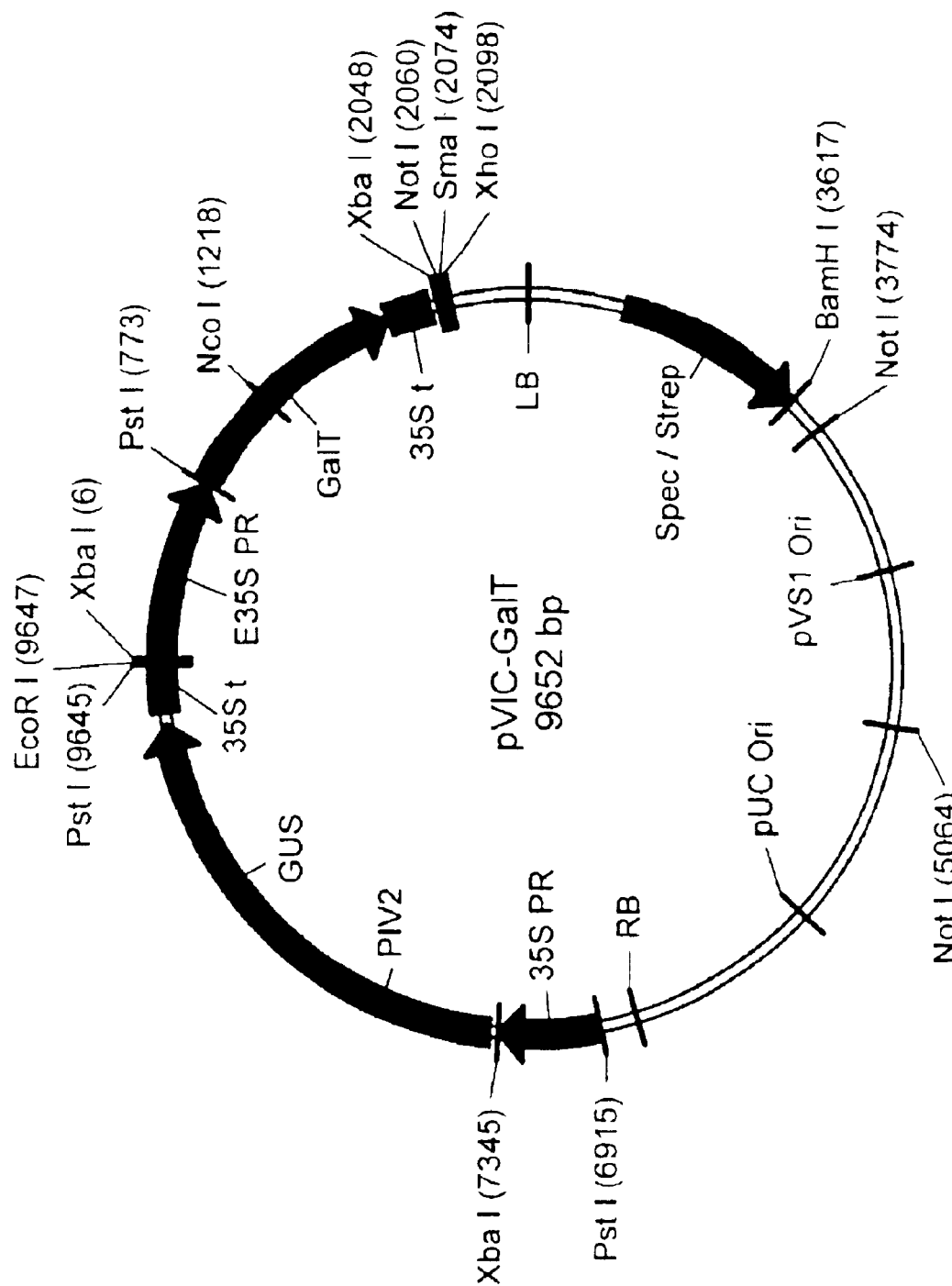

```
ACTGCAGGAAGACGACCATGACGCAATTTAATCCCGTTGATCATCGCCTACAACCCGCTCACCGGGCAATGGATTCTGGTTTCACCGCACCGCG    100
      PstI   M  T  Q  F  N  P  V  D  H  P  H  R  R  Y  N  P  L  T  G  Q  W  I  L  V  S  P  H  R      28

CTAAGCGCCCCTGGCAGGGCGCAGGAAACGCCAGCCAAACAGGTGTTACCTGCCACGATCAGATTGTTCCTCTGCCAGGTAATGTGCGGGTGAC    200
A  K  R  P  W  Q  G  A  Q  E  T  P  A  K  Q  V  L  P  A  H  D  P  D  C  F  L  C  A  G  N  V  R  V  T    62

AGGGCGATAAAAACCCGATTACACCGGGACTTACGTTTCACTAATGACTTTGCGGCTTTGATGTCTGACACGCCAGATGCGCCAGAAAGTCACGATCCG    300
G  D  K  N  P  D  Y  T  G  T  Y  V  F  T  N  D  F  A  A  L  M  S  D  T  P  D  A  P  E  S  H  D  P    95

CTGATGCGTTGCCAGAGCGCGCGGGGCACCAGCCGGGTGATCTGCTTTTCACCGGATCACAGTAAACGCTGCCAGAGCTCAGCGTTGCAGCATTGACGG    400
L  M  R  C  Q  S  A  R  G  T  S  R  V  I  C  F  S  P  D  H  S  K  T  L  P  E  L  S  V  A  A  L  T    128

AAATCGTCAAAACTGGCAGGAGCAAACCGGAGACTACCATGGGTGCAGGTTTTGAAAACAAAGGCGCGCCGATGGGCTGCTCTAA    500
E  I  V  K  T  W  Q  E  Q  T  A  E  L  G  K  T  Y  P  W  V  Q  V  F  E  N  K  G  A  P  M  G  C  S  N    162

CCCGCATCCGCACGGTCAGATTGGGCAAATAGCTTCCTGCCAGACGGTAGCGGTGAAGACCGGTTGTCGAAACAGAAATCA    600
P  H  P  H  G  Q  I  W  A  N  S  F  L  P  N  E  A  E  R  E  D  R  L  Q  K  E  Y  F  A  E  Q  K  S    195

CCAATGCTGGTGGATTATGTTCAGCGCGAGTTGGCAGACGGTAGCCGTACCGTTGTCGAAACTGGTTGCCGAAACTGGTTAGCCGTTAGCGTGCCCTGCCTTACTGGCTGCCT    700
                                                                                                                  228

GGCCGTTCGAAAGCTACTGCTGCCCCAAAGCCACGATTCGACCGCAGCGATCTGGCGCTGGCGTTGAAAAAGCT    800
W  P  F  E  T  L  L  L  P  K  A  H  V  L  R  I  T  D  L  T  D  A  Q  R  S  D  L  A  L  K  K  L    262

GACCAGTCGTTATGACAACCTCTTCCAGTGCTCTTCCCTACTCTATGGGCTGGCACGGGCGGCGCCATTTAATGGCGAGAGAATCAACACTGCAGCTG    900
T  S  R  Y  D  N  L  F  Q  C  S  F  P  Y  S  M  G  W  H  G  A  P  F  N  G  E  E  N  Q  H  W  Q  L    295

CAGGCGCACTTTATCCGCCTCTGCTGCGCTCCGCCACCGTACGTAAATTTATGGTTGGTTATGAAATGCTGGCAGAGACCCAGCGAGACCTGACCCAG    1000
H  A  K  F  Y  P  P  L  L  R  S  A  T  V  R  K  F  M  V  G  Y  E  M  L  A  E  T  Q  R  D  L  T  A    328

AACAGGCAGCAGAGCGTTGCGCGCAGTCAGTGTAAGTCGACT    1069
E  Q  A  A  E  R  L  R  A  V  S  D  I  H  F  R  E  S  G  V  *                                         348
                                          SalI

FIG. 3
```

SELECTION METHOD

The present invention relates to a selection method.

The present invention also relates to an enzyme and a nucleotide sequence coding for same that are useful in a selection method.

In particular, the present invention relates to a method for the selection (e.g. identification and/or separation) of genetically transformed cells and compounds and genetic material for use in the method.

It is well known that when a nucleotide sequence of interest ("NOI") is to be introduced into a population of cells by transformation, only a certain number of the cells are successfully transformed, i.e., only a certain number of the cells receive the NOI. It is then necessary to identify the genetically transformed cells so that these cells may be separated from the non-transformed cells in the population. For the production of transgenic plants etc., this often requires the use of a selection system that allows the regeneration and growth of the transformed (or transgenic) cells. As these transformed cells frequently constitute a minor fraction of the treated cells, compared to the majority of cells which remain untransformed, so the selection system has to be able to be effective in selecting out the transformed cells.

A common technique for a selection method includes introducing transformed cells and non-transformed cells into a medium that comprises a substance which the transformed cells are able to tolerate. In that medium the transformed cells are able to survive and grow, while the non-transformed cells are prone to growth inhibition and, in some cases, are killed.

Thus, to date, the general strategy has been to introduce a selectable gene along with the NOI(s), and then allowing the transformed cells to survive on selective media while the non-transformed cells are killed (Bowen 1993).

Typically, if a population of plant cells has been subjected to genetic transformation, selection of the transformed cells typically takes place using a selection gene which codes for antibiotic resistance or herbicide resistance. The selection gene is coupled to or co-introduced with the NOI to be incorporated into the plant in question, so that both of the two sequences are incorporated into some or all of the population of cells.

As not all of the cells may have been transformed, the cells are then cultivated on or in a medium containing the respective antibiotic or herbicide to which the genetically transformed cells are resistant by virtue of the selection gene. In this medium, the transformed cells are able to grow and thus be identified out of the total cell population, since the non-transformed cells—which do not contain the antibiotic or herbicide resistance gene in question—have an inhibited growth or even are killed.

So far, the most widely used selectable gene is the neomycin phosphotransferase II (NPTII) gene (Fraley et al. 1986) which confers resistance to the aminoglycoside antibiotics kanamycin, neomycin and G418 (Bevan et al. 1983). A number of other selective systems has been developed based on resistance to bleomycin (Hille et al. 1986), bromoxynil (Stalker et al. 1988), chloramphenicol (Fraley et al. 1983), 2,4-dichlorophenoxy-acetic acid (Streber and Willmitzer 1989), glyphosate (Shah et al. 1986), hygromycin (Waldron et al. 1985) or phosphinothricin (De Block et al. 1987).

The selection methods which rely on the use of antibiotics or herbicides suffer from a number of disadvantages. For example, there is concern amongst some people, such as environmental groups and governmental authorities, as to whether it is environmentally safe to incorporate genes coding for antibiotic resistance and/or herbicide resistance into plants and micro-organisms. This concern is of particular significance for food plants and for micro-organisms which are not designed and/or intended to be used in a closed environment (e.g. micro-organisms for use in agriculture), and also for micro-organisms which are designed for use in a closed environment but which may be released from the closed environment.

While such ecological concerns may prove unfounded, as suggested by Flavell et al., (1992), they may nevertheless lead to governmental restrictions on the use of antibiotic resistance genes in transgenic plants, and it is therefore desirable to develop new selection methods which are independent of such genes.

In addition, in some or many cases, the corresponding antibiotic or herbicide resistance genes may not be relevant to the desired transgenic trait. Also, they may be undesirable in the final product (Yoder and Goldsbrough 1994).

Thus, the use and subsequent release of selectable genes such as antibiotic resistance genes into the environment has been the target of concern among environmental authorities.

Therefore, new selection systems for the production of transgenic plants without any herbicide or antibiotic resistance genes have been developed. By way of example, these new selection systems include three selection systems based on the concept of 'positive selection' wherein transgenic cells aquire a gene which confers a metabolic advantage to those cells whilst non-transgenic cells starved rather than killed. Some of these selection systems have been reviewed by Joersbo (Joersbo 1997).

One of these positive selection methods relates to cytokinins which must be added to obtain optimal shoot regeneration. By adding cytokinin as an inactive glucuronide derivative and using a β-glucuronidase gene as selectable gene, cells which have acquired this gene by transformation are able to convert the cytokinin glucuronide to active cytokinin while untransformed cells are arrested in development (Joersho and Okkels 1996; Okkels et al. 1997).

Two other selection systems employ, as selectable agents, the carbohydrates mannose and xylose, which are not metabolised by a number of plant species (Bojsen et al. 1994). By substituting the normally employed carbohydrate with one of these compounds, cells transformed with a gene encoding an enzyme capable of converting it to a metabolisable isomer are favoured in growth while the non-transgenic cells are starved. Mannose is initially phosphorylated to mannose-6-phosphate by hexokinase present in plant cells but this compound is not metabolised any further in many plant species. Cells transformed with a phosphomannose isomerase gene are able to convert mannose-6-phosphate to the readily metabolised fructose-6-phosphate, giving these cells a metabolic advantage (Joersbo et al. 1998). Xylose can be converted to xylulose by xylose isomerase which functions as the selectable marker in this system (Haldrup 1996).

Another selection system that is not dependent on the use of herbicide and antibiotic resistance genes is described in PCT/GB98/00367. In the general method of PCT/GB98/00367, selectable transformed cells are selected from a population of cells which comprises the selectable genetically transformed cells and possible non-transformed cells. Each of the selectable genetically transformed cells comprises a first expressable nucleotide sequence and optionally a second expressable nucleotide sequence. In the selection method, a component or a metabolic derivative thereof when present in a low concentration in a medium is a nutrient for both the selectable genetically transformed cells and the non-transformed cells. In the selection method, the component or the metabolic derivative thereof when present in a high concentration in a medium is toxic to the non-transformed cells. The first nucleotide sequence codes for a gene product capable of converting the component or the metabolic derivative thereof when present in a high concentration in a medium to a nutrient for the selectable genetically transformed cells. The selection method comprises the step of introducing the population of cells to a medium, wherein the medium optionally comprises a high concentration of the component or the metabolic derivative thereof. In the selection method, the component or the metabolic derivative thereof is a source of both carbohydrate and nitrogen for the selectable genetically transformed cells. Alternatively, in the selection method if a portion of the component serves as a metabolic substrate and is metabolically converted to a derivatised substrate, then that derivatised substrate is capable of providing an allosteric effect on the gene product. In one preferred aspect, the selection method relies on the use of glucosamine.

Despite the advent of selection methods that do not necessarily rely on the use of antibiotic or herbicide resistance genes, it is still desirable to develop new methods for selecting genetically transformed cells or organisms (or parts thereof) comprising such.

According to a first aspect of the present invention there is provided:
- a selection method for selecting from a population of cells one or more selectable genetically transformed cells;
- wherein the population of cells comprises selectable genetically transformed cells and possible non-transformed cells;
- wherein each of the selectable genetically transformed cells comprises a first expressable nucleotide sequence encoding a first expression product;
- optionally wherein each of the selectable genetically transformed cells comprises an optional second expressable nucleotide sequence encoding a second expression product and/or an optional third expressable nucleotide sequence encoding a third expression product;
- wherein a component is utilisable by the selectable genetically transformed cells by action of the first expressable nucleotide sequence or the first expression product and optionally by action of the optional second expressable nucleotide sequence or the optional second expression product and/or by action of the optional third expressable nucleotide sequence or the optional third expression product;
- wherein the component can be present in an amount that is toxic to the non-transformed cells;
- the method comprising the step of introducing the population of cells to a medium, wherein the medium comprises the component and/or a derivative thereof and/or a precursor thereof and in an amount such that the component is or will be in an amount that is utilisable by the transformed cells but wherein the component is or will be in an amount that is toxic to the non-transformed cells;
  - wherein each of the first expression product and the optional second expression product and the optional third expression product is independently selected from an enzyme capable of metabolising galactose or a derivative thereof or a precursor thereof; and
  - wherein the component and/or the derivative thereof and/or the precursor thereof is galactose or a derivative thereof or a precursor thereof.

For convenience, we sometimes refer to the selection method of the present invention as being the "galactose selection method". However, it is to be understood that the method of the present invention is not necessarily limited to galactose as being the component or the precursor of the component that enables workers to select transformed cells over non-transformed cells. However, and as will become apparent, in a preferred embodiment galactose is a preferred component or precursor for the component and/or galactose-1-phosphate is a preferred component or derivative thereof.

The component may be any suitable chemical compound, product, molecule etc.

The term "utilisable" as used herein with reference to the present invention (e.g. "the component is utilisable by the selectable genetically transformed cells") means that the component can be processed in a non-adverse or non-detrimental fashion by the selectable genetically transformed cells. Thus, the term includes metabolising (such as metabolising in a beneficial manner), detoxifying, etc. For some applications, the term "utilisable" may mean at least "metabolisable". For some applications, the term "utilisable" may mean at least "detoxifiable". Here, the term "detoxifiable" means capable of being converted to one or more derivatives that do not have an adverse effect on the transformed cell. An example of an adverse effect is growth inhibition. These derivatives may or may not accumulate in the cells. In addition, or in the alternative, these derivatives may or may not be fully metabolisied by the transformed cell.

The derivative of the component can be any suitable derivative—such as a chemical derivative, a metabolic derivative, etc.

For some applications, preferably the derivative of the component is at least a metabolic derivative.

The precursor of the component can be any suitable precursor—such as a metabolic precursor, etc.

For some applications, preferably the precursor of the component is at least a metabolic precursor.

The action of the the first expressable nucleotide sequence or the first expression product and optionally the optional second expressable nucleotide sequence or the optional second expression product and/or the optional third expressable nucleotide sequence or the optional third expression product may be direct or indirect. Here, indirect action may mean that the first expression product or the optional second expression product or the optional third expression product converts a precursor of the component to, for example, the component or even another precursor thereof or a derivative thereof. However, the component that is present or is produced by direct or indirect action is or will be in an amount that is utilisable by the transformed cells but in an amount that is toxic to the non-transformed cells.

According to a second aspect of the present invention there is provided
- a composition comprising a population of cells comprising selectable genetically transformed cells and possible non-transformed cells; and a medium;
- wherein each of the selectable genetically transformed cells comprises a first expressable nucleotide sequence encoding a first expression product;
- optionally wherein each of the selectable genetically transformed cells comprises an optional second expressable nucleotide sequence encoding a second expression product and/or an optional third expressable nucleotide sequence encoding a third expression product;
- wherein a component is utilisable by the selectable genetically transformed cells by action of the first expressable nucleotide sequence or the first expression product and optionally by action of the optional second expressable nucleotide sequence or the optional second expression product and/or by action of the optional third expressable nucleotide sequence or the optional third expression product;

wherein the component can be present in an amount that is toxic to the non-transformed cells;

wherein the medium comprises the component and/or a derivative thereof and/or a precursor thereof and in an amount such that the component is or will be in an amount that is utilisable by the transformed cells but wherein the component is or will be in an amount that is toxic to the non-transformed cells;

wherein each of the first expression product and the optional second expression product and the optional third expression product is independently selected from an enzyme capable of metabolising galactose or a derivative thereof or a precursor thereof; and wherein the component and/or the derivative thereof and/or the precursor thereof is galactose or a derivative thereof or a precursor thereof.

According to a third aspect of the present invention there is provided population of cells comprising selectable genetically transformed cells and possible non-transformed cells;

wherein each of the selectable genetically transformed cells comprises a first expressable nucleotide sequence encoding a first expression product;

optionally wherein each of the selectable genetically transformed cells comprises an optional second expressable nucleotide sequence encoding a second expression product and/or an optional third expressable nucleotide sequence encoding a third expression product;

wherein a component is utilisable by the selectable genetically transformed cells by action of the first expressable nucleotide sequence or the first expression product and optionally by action of the optional second expressable nucleotide-sequence or the optional second expression product and/or by action of the optional third expressable nucleotide sequence or the optional third expression product;

wherein the component can be present in an amount that is toxic to the non-transformed cells;

wherein each of the first expression product and the optional second expression product and the optional third expression product is independently selected from an enzyme capable of metabolising galactose or a derivative thereof or a precursor thereof; and wherein the component and/or the derivative thereof and/or the precursor thereof is galactose or a derivative thereof or a precursor thereof.

According to a fourth aspect of the present invention there is provided a selectable genetically transformed cell comprising a first expressable nucleotide sequence encoding a first expression product; and optionally a second expressable nucleotide sequence encoding a second expression product and/or a third expressable nucleotide sequence encoding a third expression product;

wherein a component is utilisable by the selectable genetically transformed cells by action of the first expressable nucleotide sequence or the first expression product and optionally by action of the optional second expressable nucleotide sequence or the optional second expression product and/or by action of the optional third expressable nucleotide sequence or the optional third expression product;

wherein the component can be present in an amount that is toxic to the non-transformed cells;

wherein each of the first expression product and the optional second expression product and the optional third expression product is independently selected from an enzyme capable of metabolising galactose or a derivative thereof or a precursor thereof; and wherein the component and/or the derivative thereof and/or the precursor thereof is galactose or a derivative thereof or a precursor thereof.

According to a fifth aspect of the present invention there is provided an organism comprising a selectable genetically transformed cell according to the present invention.

According to a sixth aspect of the present invention there is provided a construct for genetically transforming a non-transformed cell to produce a selectable genetically transformed cell;

the construct comprising a first expressable nucleotide sequence encoding a first expression product; and optionally a second expressable nucleotide sequence encoding a second expression product and/or a third expressable nucleotide sequence encoding a third expression product;

wherein a component is utilisable by the selectable genetically transformed cells by action of the first expressable nucleotide sequence or the first expression product and optionally by action of the optional second expressable nucleotide sequence or the optional second expression product and/or by action of the optional third expressable nucleotide sequence or the optional third expression product;

wherein the component can be present in an amount that is toxic to the non-transformed cells;

wherein each of the first expression product and the optional second expression product and the optional third expression product is independently selected from an enzyme capable of metabolising galactose or a derivative thereof or a precursor thereof; and wherein the component and/or the derivative thereof and/or the precursor thereof is galactose or a derivative thereof or a precursor thereof.

According to a seventh aspect of the present invention there is provided a vector comprising the construct according to the present invention.

According to an eighth aspect of the present invention there is provided a plasmid comprising the construct according to the present invention.

According to a ninth aspect of the present invention there is provide a kit comprising a construct according to the present invention or a vector according to the present invention or a plasmid according to the present invention for genetically transforming a non-transformed cell to produce a selectable genetically transformed cell; and a medium.

According to a tenth aspect of the present invention there is provided a plant or plant cell comprising one or more heterologous enzymes, wherein the heterologous enzymes are any one or more of galactokinase (EC 2.7.1.6), UTP-dependent pyrophosphorylase (EC 2.7.7.10), UDP-glucose-dependent uridylyltransferase (EC 2.7.7.12), UDP-galactose epimerase (EC 5.1.3.2).

Here the term "heterologous enzymes" includes enzymes that are derived from a different species or even a different cell. The term also includes enzymes (which may or may not be native to the cell) which are expressed by recombinant nucleotide sequences. The term also includes homologous enzymes that have been expressed by homologous coding sequences but when under the control of heterologous promoters. Here the term "heterologous promoters" means promoters that are not naturally associated with the coding sequence in question.

According to an eleventh aspect of the present invention there is provided a feed, foodstuff or food prepared from or comprising the aspects of the present invention.

According to a twelfth aspect of the present invention there is provided the use of any one or more of galactokinase (EC 2.7.1.6), UTP-dependent pyrophosphorylase (EC 2.7.7.10), UDP-glucose-dependent uridylyltransferase (EC 2.7.7.12), UDP-galactose epimerase (EC 5.1.3.2) as a selection means for selecting a genetically transformed cell over a non-transformed cell.

According to a thirteenth aspect of the present invention there is provided the use of any one or more of a nucleotide sequence coding for galactokinase (EC 2.7.1.6), UTP-dependent pyrophosphorylase (EC 2.7.7.10), UDP-glucose-dependent uridylyltransferase (EC 2.7.7.12), UDP-galactose epimerase (EC 5.1.3.2) for providing a selection means for selecting a genetically transformed cell over a non-transformed cell.

According to a fourteenth aspect of the present invention there is provided the use of any one or more of galactose, galactose-1-phosphate, UDP-galactose, or derivatives thereof as a selection means for selecting a genetically transformed cell over a non-transformed cell.

According to a fifteenth aspect of the present invention there is provided a selection method for selecting from a population of cells one or more selectable genetically transformed cells, wherein the population of cells comprises selectable genetically transformed cells and possible non-transformed cells;

wherein each of the selectable genetically transformed cells comprises a first expressable nucleotide sequence encoding a first expression product;

optionally wherein each of the selectable genetically transformed cells comprises an optional second expressable nucleotide sequence encoding a second expression product and/or an optional third expressable nucleotide sequence encoding a third expression product;

the method comprising the step of preparing the population of cells by transforming some or all of the cells in an initial population of cells containing non-transformed cells with a heterologous nucleotide sequence so as to form the population of cells containing one or more selectable genetically transformed cells; and selecting at least one of the selectable genetically transformed cells;

wherein the heterologous nucleotide sequence is any one or more of the first expressable nucleotide sequence, the optional second expressable nucleotide sequence or the optional third expressable nucleotide sequence;

wherein each of the first expression product and the optional second expression product and the optional third expression product is independently selected from an enzyme capable of metabolising galactose or a derivative thereof or a precursor thereof.

Here, the term "heterologous nucleotide sequence" includes nucleotide sequences that are derived from a different species or even a different cell. The term also includes nucleotide sequences (which may or may not be native to the cell) that have been prepared by use of recombinant DNA techniques. The term also includes native nucleotide sequences but when under the control of heterologous promoters. Here the term "heterologous promoters" means promoters that are not naturally associated with the nucleotide sequence in question.

In one preferred aspect, the selectable genetically transformed cell/cells is/are in vitro within a culture.

In an alternative preferred aspect, the selectable genetically transformed cell/cells is/are in vivo within an organism.

Preferably the selectable genetically transformed cell/cells is/are selectable genetically transformed plant cell/cells.

Preferably an additional nucleotide sequence is present and wherein the additional nucleotide sequence codes for a nucleotide sequence of interest ("NOI").

Preferably the organism is a plant.

Preferably the plant is capable of providing a foodstuff for humans or animals.

In an alternative preferred aspect, the plant is capable of providing a commodity for humans—such as cotton, tobacco etc.

Preferably the plant (or part thereof, including cells thereof) is a monocot or a dicot (including legumes).

In a preferred aspect, the plant is any one of rape seed, potato or maize.

For some applications, preferably the component is present in the medium.

For some applications, preferably the component is prepared in situ in the cell from a precursor that was present in the medium.

If the component is prepared in situ in the cell from a precursor that was present in the medium, then galactose is a preferred component or precursor for the component and/or a preferred component or derivative thereof is galactose-1-phosphate.

More preferably, if the component is prepared in situ in the cell from a precursor that was present in the medium, then galactose is a preferred precursor for the component and/or a preferred component is galactose-1-phosphate.

Thus, in each aspect of the present invention, a precursor for the component is preferably metabolically converted to the component by the transformed cell.

When the component or the derivative thereof or precursor thereof is present in the medium then preferably the component or the derivative thereof or precursor thereof is present in an amount that does not detrimentally affect a major proportion of the transformed cells.

Preferably, when the component or the derivative thereof or precursor thereof is present in the medium then the component or the derivative thereof or precursor thereof is present in an amount that does not detrimentally affect substantially most of the transformed cells.

More preferably, when the component or the derivative thereof or precursor thereof is present in the medium then the component or the derivative thereof or precursor thereof is present in an amount that does not detrimentally affect substantially all of the transformed cells.

In a further aspect, in some cases the medium need not contain any added quantities of the component or the derivative or precursor thereof according to the present invention.

Preferably, however, the medium contains added quantities of the component or the derivative or precursor thereof according to the present invention.

For some applications, if carbohydrates are also present in addition to the component or the derivative thereof or the precursor therefor then preferably the carbohydrates are present in amounts that do not affect substantially the effect of the component or the derivative thereof or the precursor therefor. Typically, said levels of carbohydrate(s) will be low levels.

Other aspects of the present invention include:

The use of any one or more of galactose, galactose-1-phosphate, UDP-galactose, or any derivative thereof, as a selection means for selecting a genetically transformed cell over a non-transformed cell.

The use of any one or more of a nucleotide sequence coding for any one or more of galactokinase (EC 2.7.1.6). UTP-dependent pyrophosphorylase (EC 2.7.7.10), UDP-glucose-dependent uridylyltransferase (EC 2.7.7.12), UDP-galactose epimerase (EC 5.1.3.2) for providing a selection means for selecting a genetically transformed cell over a non-transformed cell.

The use of any one or more of galactokinase (EC 2.7.1.6), UTP-dependent pyrophosphorylase (EC 2.7.7.10), UDP-glucose-dependent uridylyltransferase (EC 2.7.7.12), UDP-galactose epimerase (EC 5.1.3.2) for providing a selection means for selecting a genetically transformed cell over a non-transformed cell.

In the above aspects, the phrase "selecting a genetically transformed cell over a non-transformed cell" can be alternatively expressed as "selecting a genetically transformed cell from one or more non-transformed cells".

Preferably, any one or more of the first, second or third expressable nucleotide sequence and/or any one or more of the first, second or third expression product (such as any one or more of the enzymes galactokinase, UTP-dependent pyrophosphorylase, UDP-glucose dependent uridylyltransferase and UDP-galactose epimerase and/or nucleotide sequences coding for same) are, for example, obtainable from any one or more of: *E. coli* (CE Vorgias, H-G Lemaire, K S Wilson 1991. Protein Expr. and Pur. 2, 330–338); *Saccharomyces* sp. (R A Darrow, R Rodstrom 1968. Biochemistry 7, 1645–1654; M A Schell, D B Wilson 1977. J. Biol. Chem. 252, 1162–1166); *Streptomyces coelicolor* A3 (B D Wilson, D S Hogness 1966. in Methods in Enzymol. vol. 8, pp. 229–240, Academic Press, San Diego); Tetrahymena thermophila (J E Lavine, E Cantlay, C T Roberts, D E Morse 1982. Biochim. Biophys. Acta 717, 76–85); *Clostridium* pasterianum (F Daldal, J Applebaum 1985. J. Mol. Biol. 186, 533–545); *Kluveromyces* lactis (M I Riley, R C Dickson 1984. J. Bacteriol. 158, 705–712); *Vicia faba; Petunia* sp.; and mammals eg. Chinese hampster (B Talbot, J-P Thirion 1982. Int. J. Biochem. 14, 719–725), human (WO 96/09374).

According to one aspect of the present invention there is provided a selection system that uses a component or a precursor therefor or a derivative thereof for selecting at least one genetically transformed cell from a population of cells, wherein the at least one genetically transformed cell is transformed with a nucleotide sequence which encodes an expression product capable of utilising the component but wherein the component toxic to non-transformed cells.

According to another aspect of the present invention there is provided a selection system for selecting at least one genetically transformed cell from a population of cells in a medium, wherein the at least one genetically transformed cell is transformed with a nucleotide sequence which encodes an expression product capable of converting a component or precursor therefor or a derivative thereof, that is present in the medium that provides the component at an amount that is toxic to non-transformed cells but is utilisable (e.g. metabolitisable and/or detoxifiable) by the at least one transformed cell. The term "cells" is intended to refer to any type of cells from which individual genetically transformed cells may be identified and isolated using the method of the invention. Examples of such cells typically include cells of plants that have a commercial worth—such as crops useful for food or feed production. If desired, other plant cells can be transformed. The term "cells" is also meant to encompass protoplasts, i.e. the protoplasm of a cell enclosed in a membrane but without a cell wall. While it is contemplated that the selection method of the present invention may be used for any type of cell, the method has been found to be particularly suitable for the selection of genetically transformed plant cells.

The term "population of cells" refers to any group of cells which has been subjected to genetic transformation and from which it is desired to identify those cells which have been genetically transformed and to isolate the genetically transformed cells from non-genetically transformed cells. The population may, for example, be a tissue, an organ or a portion thereof, a population of individual cells in or on a substrate, such as a culture of plant cells, for example a population of cells in a solution or suspension, or a whole organism, such as an entire plant.

The term "selecting" refers to the process of identifying and/or isolating the genetically transformed cells from the non-genetically transformed cells using the method of the present invention.

The term "medium" includes any medium that is capable of sustaining the viability (such as growth) of the transformed cells while inhibiting or killing the non-transformed cells. For example, the medium may comprise typical ingredients of a growth medium but wherein those ingredients are in such an amount that the transformed cells are selectively grown. In accordance with the present invention, the medium may typically comprise at least a component, or a precursor therefor or a derivative thereof, according to the present invention.

The term "toxic" as used herein in relation to the non-transformed cells means that the component or derivative thereof or a precursor thereof has an adverse effect on the non-transformed cells or is metabolised to a derivative that has an adverse effect on the non-transformed cells. An example of an adverse effect is growth inhibition. The term also includes death of the non-transformed cells.

The term "genetically transformed" includes transformation using recombinant DNA techniques.

The term "introducing the population of cells to a medium" means adding the population of cells to the medium or vice versa.

The component of the present invention may be derived from a precursor therefor.

Preferably, the precursor is present in a medium and the precursor is processed by the cells to the component—such as by use of naturally occuring enzymes and/or by use of heterologous enzymes (such as those expressed by recombinant DNA).

The term "vector" includes expression vectors and transformation vectors.

The term "expression vector" means a construct capable of in vivo or in vitro expression.

The term "transformation vector" means a construct capable of being transferred into a species—such as a plant by use of, for example, direct gene transfer techniques (such as particle gun techniques for monocot transformation).

The term "tissue" includes tissue per se and organ.

The term "organism" in relation to the present invention includes any organism that could comprise the nucleotide sequence coding for the enzyme according to the present invention and/or products obtained therefrom, and/or wherein the nucleotide sequence according to the present invention can be expressed when present in the organism.

Preferably the organism is a plant.

The term "transgenic organism" in relation to the present invention includes any organism that comprises the nucleotide sequence coding for the enzyme according to the present invention and/or products obtained therefrom, and/or wherein the nucleotide sequence according to the present invention can be expressed within the organism.

Preferably the nucleotide sequence is incorporated in the genome of the organism.

Preferably the transgenic organism is a plant. In a highly preferred embodiment, the transgenic organism (or part thereof) does not comprise the combination of a promoter and at least one of the first nucleotide sequence coding for the first enzyme according to the present invention, the second nucleotide sequence coding for the second enzyme according to the present invention and the third nucleotide sequence coding for the third enzyme according to the present invention, wherein both the promoter and the nucleotide sequence are native to that organism (or part thereof) and are in their natural environment. Thus, in this highly preferred embodiment, the present invention does not cover at least one of a native first nucleotide sequence coding for the first enzyme according to the present invention, a native second nucleotide sequence coding for the second enzyme according to the present invention and a native nucleotide sequence coding for the third enzyme according to the present invention in its natural environment when it is under the control of its native promoter which is also in its natural environment. In addition, in this highly preferred embodiment, the present invention does not cover the native enzyme according to the present invention (namely any one of the first enzyme according to the present invention, the second enzyme according to the present invention, the third enzyme according to the present invention) when it is in its natural environment and when it has been expressed by its native nucleotide coding sequence which is also in its natural environment and when that nucleotide sequence is under the control of its native promoter which is also in its natural environment. In other words, it is preferred that the nucleotide sequence is heterologous to the organism and/or is under the control of a heterologous promoter.

In accordance with a highly preferred aspect of the present invention, the component and/or the derivative thereof and/or the precursor thereof are not prepared in situ in the medium—i.e. they are actual ingredients that are added to make up the medium.

In one aspect of the present invention, the one or more components or derivatives thereof can act as a nutrient for the transformed cells.

However, in one aspect, the one or more components or derivatives thereof need not act as the only possible nutrient for the transformed cells. Examples of other nutrients that may be used include any one or more of carbohydrates, sucrose, maltose, and other energy sources. In addition, or in the alternative, the transformed cells may be grown on other suitable growth media which do not contain the one or more components or derivatives. In this latter case, the transformed cells will not be selectable due to the presence of just the sequences of the present invention—but they could also be selectable due to the presence of other selectable sequences.

Here, the term "nutrients" includes a substance that is capable of providing directly or indirectly (e.g. via a metabolite thereof) energy or atoms or molecules that are beneficially useful for maintenance and/or growth and/or reproduction etc. of the cell, tissue, organ or organism.

For example, the term includes a substrate that can be beneficially metabolised and/or beneficially utilised in a metabolic pathway to enable the transformed cells to grow, to proliferate or to be maintained in a viable form. Here, "beneficial" as used in relation to the present invention means at least not causing an adverse, detrimental effect to the transformed cells.

In accordance with the present invention, a non-transformed cell is a cell that does not comprise at least one of the first nucleotide sequence according to the present invention, the second nucleotide sequence according to the present invention and the third nucleotide sequence according to the present invention.

The non-transformed cell of the present invention may even be a previously transformed cell that does not comprise at least any one of the first nucleotide sequence according to the present invention, the second nucleotide sequence coding according to the present invention and the third nucleotide sequence according to the present invention. The non-transformed cell of the present invention can, however, contain one or more heterologous nucleotide sequences, or one or more homologous nucleotide sequences under the control of one or more heterologous transcriptional control elements.

The transformed cell of the present invention may contain one or more heterologous nucleotide sequences, or one or more homologous nucleotide sequences under the control of one or more heterologous transcriptional control elements.

In a highly preferred embodiment, the first nucleotide sequence is not in its natural environment. In this regard, the first nucleotide sequence may not be native (i.e. foreign) to the cell or organism. In addition, the first nucleotide sequence may be native to the cell or organism but wherein the first nucleotide sequence is operably linked to a promoter that is heterologous to the first nucleotide sequence.

In accordance with the present invention there may be a plurality of first nucleotide sequences and/or second nucleotide sequences and/or third nucleotide sequences.

The or each first nucleotide sequence may be independently selected from DNA or RNA. Preferably, the or each first nucleotide sequence is DNA. More preferably, the or each first nucleotide sequence is recombinant DNA.

The second nucleotide sequence may be independently selected from DNA or RNA. Preferably, the or each second nucleotide sequence is DNA. More preferably, the or each second nucleotide sequence is recombinant DNA.

The third nucleotide sequence may be independently selected from DNA or RNA. Preferably, the or each third nucleotide sequence is DNA. More preferably, the or each third nucleotide sequence is recombinant DNA.

The term "recombinant DNA" means DNA prepared by at least one step that utilises at least one recombinant DNA technique.

Thus, in a first broad aspect the present invention relates inter alia to the use of at least one nucleotide sequence encoding an expression product that affects galactose or a derivative thereof or a precursor thereof as a selective agent for the selection of transgenic cells, tissues, organs, organisms (such as plants).

In a second broad aspect the present invention relates inter alia to the use of the expression product of at least one nucleotide sequence that affects galactose or a derivative thereof or a precursor thereof as a selective agent for the selection of transgenic cells, tissues, organs, organisms (such as plants).

In a third broad aspect the present invention relates inter alia to galactose or a derivative thereof or a precursor thereof as a selective agent for the selection of transgenic cells, tissues, organs, organisms (such as plants).

Galactose is a hexose which has been demonstrated to be toxic to most plant species (eg. Farkas 1954; Hughes and Street 1974; Roberts et al. 1971).

Galactose has optical isomeric forms and can occur as a linear or a cyclic structure.

An example of a galactose molecule can be pictorially represented as:

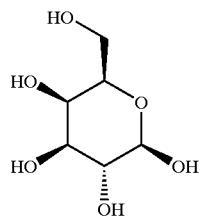

Preferably the component is galactose, preferably D-galactose.

If the medium of the present invention comprises a precursor of galactose then preferably the precursor is capable of liberating free galactose or a derivative thereof.

Preferably the precursor is capable of liberating free galactose.

More preferably the precursor is capable of liberating free D-galactose.

If the medium of the present invention comprises a precursor of galactose then preferably one or more enzymes are present which can liberate free galactose or a derivative thereof from the precursor.

Preferably if the medium of the present invention comprises a precursor of galacatose then preferably one or more enzymes are present which can liberate free D-galactose.

Preferably the enzyme(s) is at least a galactosidase.

Preferably the enzyme(s) is/are selected from one or more of α-galactosidases or β-galactosidases.

The enzyme can be present in the medium already or it can be prepared by the medium itself. Alternatively, the enzyme can be prepared by the transformed cell. Here, the enzyme can be native to the cell or it can be heterologous to the cell. The transformed cell may also comprise an additional nucleotide sequence coding for an enzyme capable of releasing galactose from a precursor thereof.

Peferable examples of precursors of galactose include galactose containing compounds-such as lactoses, melibioses, raffinoses, stachyoses, verbascoses and galactinols.

More preferable precursors of galactose include α-lactose (β-D-galactopyranosyl [1→4]-α-D-glucose, milk sugar), β-lactose, melibiose (6-O-α-D-galacto-pyranosyl-D-glucose), raffinose, stachyose, verbascose and galactinol and any other substrate which liberates free D-galactose upon hydrolysis by either α-galactosidases or β-galactosidases.

Other examples of potentially useful precursors for use in the galactose selection method of the present invention are chemically derivatised forms of galactose, preferably chemical derivatives of D-galactose, from which free galactose can be liberated by use of appropriate techniques, such as enzyme action. By way of example, suitable chemical derivaties are D-galactose pentaacetate and D-galactose methyl galactoside.

Alternatively or in addition, the medium may comprise a derivative of galactose.

Preferable examples of such a derivative include galactose-1-phosphate and UDP-galactose.

Galactose-1-phosphate can be pictorially represented as:

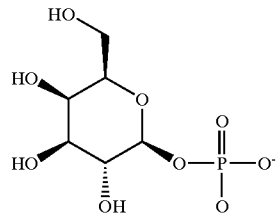

UDP-galactose can be pictorially represented as:

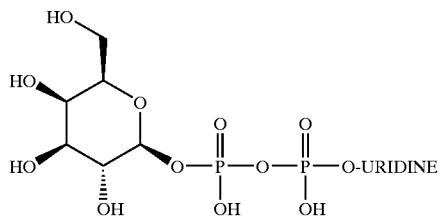

More preferable examples of such a derivative include D-galactose-1-phosphate and UDP-D-galactose.

Preferably the component is galactose-1-phosphate.

Preferably the precursor for the component is galactose.

Preferably each of the first expression product; the second expression product and the third expression product is independently selected from galactokinase (EC 2.7.1.6), UTP-dependent pyrophosphorylase (EC 2.7.7.10), UDP-glucose-dependent uridylyltransferase (EC 2.7.7.12), UDP-galactose epimerase (EC 5.1.3.2).

Preferably each of the first expression product; the second expression product and the third expression product is independently selected from galactokinase (EC 2.7.1.6) obtainable from Petunia, yeast and other microorganisms, Vicia faba, Phaseolus areus, barley or corn, UTP-dependent pyrophosphorylase (EC 2.7.7.10) obtainable from Petunia, UDP-glucose-dependent uridylyltransferase (EC 2.7.7.12) obtainable from yeast and other microorganisms, UDP-galactose epimerase (EC 5.1.3.2) obtainable from Petunia, yeast and other microorganisms, fenugreek, wheat, sugarcane and various trees.

Preferably, each of the first expressable nucleotide sequence, the second expressable nucleotide sequence and the third expressable nucleotide is independently selected from expressable nucleotide sequences coding for any one or more of galactokinase (EC 2.7.1.6), UTP-dependent pyrophosphorylase (EC 2.7.7.10), UDP-glucose-dependent uridylyltransferase (EC 2.7.7.12), UDP-galactose epimerase (EC 5.1.3.2).

Preferably, each of the first expressable nucleotide sequence, the second expressable nucleotide sequence and the third expressable nucleotide is independently selected from expressable nucleotide sequences coding for any one or more of galactokinase (EC 2.7.1.6) obtainable from Petunia, yeast and other microorganisms, Vicia faba, Phaseolus areus, barley or corn. UTP-dependent pyrophosphorylase (EC 2.7.7.10) obtainable from Petunia, UDP-glucose-dependent uridylyltransferase (EC 2.7.7.12) obtainable from yeast and other microorganisms, UDP-galactose epimerase (EC 5.1.3.2) obtainable from Petunia, yeast and other microorganisms, fenugreek, wheat, sugar cane and various trees.

In one preferred aspect of the present invention, the transformed cells comprise the first expressable nucleotide sequence but not the optional second expressable nucleotide sequence and not the optional third expressable nucleotide sequence.

In this aspect of the present invention, preferably the first expressable nucleotide sequence is a nucleotide sequence coding for UDP-galactose epimerase (EC 5.1.3.2) or UDP-glucose-dependent uridylyltransferase (EC 2.7.7.12). In this aspect, preferably the medium comprises UDP-galactose and/or galactose-1-phosphate, or derivatives thereof.

In one preferred aspect of the present invention, the transformed cells comprise the first expressable nucleotide sequence and the optional second expressable nucleotide sequence, but not the optional third expressable nucleotide sequence.

In this aspect of the present invention, preferably the first expressable nucleotide sequence is a nucleotide sequence that codes for UDP-galactose epimerase, and the second expressable nucleotide sequence is a nucleotide sequence that codes for UTP-dependent pyrophosphorylase (EC 2.7.7.10) and/or UDP-glucose-dependent uridylyltransferase (EC 2.7.7.12). In this aspect, preferably the medium comprises at least galactose-1-phosphate. For example, the medium may comprise galactose-1-phosphate and UDP-galactose, or derivatives thereof.

In one preferred aspect of the present invention, the transformed cells comprise the first expressable nucleotide sequence and the optional third expressable nucleotide sequence, but not the optional second expressable nucleotide sequence.

In this aspect of the present invention, preferably the first expressable nucleotide sequence is a nucleotide sequence that codes for UDP-galactose epimerase, and the third expressable nucleotide sequence is a nucleotide sequence that codes for galactokinase (EC 2.7.1.6). In this aspect, preferably the medium comprises at least galactose. For example, the medium may comprise galactose and UDP-galactose, or derivatives thereof.

In one preferred aspect of the present invention, the transformed cells comprise the first expressable nucleotide sequence, the optional second expressable nucleotide sequence, and the optional third expressable nucleotide sequence.

In this aspect of the present invention, preferably the first expressable nucleotide sequence is a nucleotide sequence that codes for UDP-galactose epimerase, the second expressable nucleotide sequence is a nucleotide sequence that codes for UTP-dependent pyrophosphorylase (EC 2.7.7.10) and/or UDP-glucose-dependent uridylyltransferase (EC 2.7.7.12), and the third expressable nucleotide sequence is a nucleotide sequence that codes for galactokinase (EC 2.7.1.6). In this aspect, preferably the medium comprises at least galactose, or derivatives thereof. For example, the medium may comprise galactose and galactose-1-phosphate, or derivatives thereof. For example, the medium may comprise galactose and UDP-galactose, or derivatives thereof. For example, the medium may comprise galactose, galactose-1-phosphate and UDP-galactose, or derivatives thereof.

In accordance with the present invention, the medium can comprise one or more of the component, the derivative thereof and the precursor.

In order to prepare any one or more of the transformed cells, tissues, organs and organisms according to the present invention, the first expressable nucleotide sequence, the optional second expressable nucleotide sequence and the optional third expressable nucleotide sequence can be introduced into the original non-transformed cells by use of any one or more of a single construct, a single plasmid, or a single vector. Alternatively, the first expressable nucleotide sequence, the optional second expressable nucleotide sequence and the optional third expressable nucleotide sequence can be introduced into the original non-transformed cells by use of any one or more of: two or more constructs, two or more plasmids, or two or more vectors.

In accordance with the present invention any one or more of the first nucleotide sequence, the second nucleotide sequence and the third nucleotide sequence may comprise an intron.

In this respect, the presence of the intron within the coding portions of the first nucleotide sequence and/or the second nucleotide sequence and/or the third nucleotide sequence may inactivate the expression products thereof vis-a-vis a prokaryote, such as a prokaryotic vector system used to generate the transformed cells, tissue, organs or organism.

The present invention therefore provides a method for selecting genetically transformed cells—such as cells into which a NOI has been incorporated—by providing the transformed cells with a selective advantage.

The method of the present invention is not dependent on the preparation of genetically transformed plants containing as a selection means a nucleotide sequence coding for antibiotic or herbicide resistance. Nevertheless, the method of the present invention can be used in conjunction with those earlier selection methods should the need arise—if for example it is desirable to prepare cells that have been or are to be transformed with a number of NOIs.

Also, the selection method of the present invention can be used in conjunction with one or more other known selection methods, such as those that are described in WO 93/05163 (the contents of which are incorporated herein by reference) and/or WO 94/20627 (the contents of which are incorporated herein by reference) and/or PCT/GB98/00367 (the contents of which are incorporated herein by reference), should the need arise—if for example it is desirable to prepare cells that have been transformed with a number of NOIs.

In addition, the selection method of the present invention can be used in conjunction with one or more other selection methods according to the present invention should the need arise—if for example it is desirable to prepare cells that have been transformed with a number of NOIs.

A further beneficial use of a combination of selection methods according to the present invention results in a very efficient multiple screening technique. In this regard, and by way of example, the medium in the first screen utilising the selection method of the present invention would contain added low amounts of the component or the derivative thereof. With this first screen, selectable transformed cells are selected over at least the majority of the non-transformed cells. Then should—for example—any non-transformed cells be accidentally be carried over in that first screen then a second screen can be carried out. In the second screen the selected population of cells are subjected to a second selection method according to the present invention but wherein the component or the derivative thereof is present in the medium in a high concentration. In the second screen, predominantly the transformed cells would remain viable.

With this combined aspect of the present invention, the population of cells of the earlier aspects of the present invention can therefore be a pre-selected (e.g. pre-screened) population of cells, wherein the population of cells has been prior selected by one or more selection methods, such as those according to the present invention.

This combined aspect of the present invention can be alternatively expressed as: a selection method for selecting from a population of cells one or more selectable genetically transformed cells, wherein the population of cells comprises selectable genetically transformed cells and possible non-transformed cells; wherein each of the selectable genetically transformed cells comprises a first expressable nucleotide sequence encoding a first expression product; optionally wherein each of the selectable genetically transformed cells comprises an optional second expressable nucleotide sequence encoding a second expression product and/or an optional third expressable nucleotide sequence encoding a third expression product; wherein a component is utilisable by the selectable genetically transformed cells by action of the first expressable nucleotide sequence or the first expression product and optionally by action of the optional second expressable nucleotide sequence or the optional second expression product and/or by action of the optional third expressable nucleotide sequence or the optional third expression product; wherein the component can be present in an amount in a medium that is toxic to the non-transformed cells; the method comprising (a) the step of introducing the population of cells to a medium; wherein the component is or will be in such an amount that is utilisable by the transformed cells but in an amount that is toxic to the non-transformed cells; wherein each of the first expression product and the optional second expression product and the optional third expression product is independently selected from an enzyme capable of metabolising galactose or a derivative thereof or a precursor thereof; and wherein the component and/or the derivative thereof and/or the precursor thereof is galactose or a derivative thereof or a precursor thereof; and (b) a subsequent step of introducing at least portion of the transformed cells to a medium that comprises a higher concentration of the component or the derivative thereof or precursor thereof.

The present invention also encompasses compositions and kits useful for this combined aspect of the present—such as the nucleotide sequence or expression product thereof according to the present invention, a first medium containing no component or derivative thereof, and a second medium comprising a high concentration of the component or derivative thereof.

Furthermore, the selection method of the present invention can be used in conjunction (such as sequentially) with further selection methods wherein those further selection methods are a combination of one or more other selection methods according to the present invention and one or more known selection methods—such as those that are dependent on antibiotic or herbicide resistance and/or those that are disclosed in WO 93/05163 and/or WO 94/20627.

In the selection methods of WO 93/05163 and/or WO 94/20627, the manA gene from *Escherichia coli*, which encodes mannose-6-phosphate isomerase (E.C. 5.3.2.8.), was employed as a selectable marker. This selection marker is suitable for inter alia the transformation of *Solanum tuberosum*, conferring positive selection in the presence of mannose. In more detail, the coding region of manA was ligated into a CaMV 35S expression cassette, and introduced into a binary vector for plant transformation mediated by *Agrobacterium tumefaciens*. To allow comparison of kanamycin selection with selection on mannose, the vector also contained a gene for kanamycin resistance, nptII. In order to identify transformants, the construction also contained the B-glucuronidase histochemical marker, uidA. Stable integration of the mannose gene was shown by Southern blotting. Extracts from plants transformed with this construct, and selected on mannose, were shown to have specific activities for mannose-6-phosphate isomerase some five hundred fold those of control plants. Expression of mana in transformed cells relieved the metabolic paralysis, usually caused by mannose, while also allowing it to serve as a source of carbohydrate for transformants. These effects combined to impose a stringent selection pressure in favour of transformed cells, which allowed the recovery of transformants with a very low frequency of escapes. The percentage of shoots which were shown to be transgenic after selection on mannose was approximately twice that of shoots selected on kanamycin. The transformants selected on mannose have proven to be stable over three generations of plants propagated from tubers.

Hence, the population of cells of the earlier aspects of the present invention can therefore be a pre-selected (e.g. pre-screened) population of cells, wherein the population of cells has been prior selected by one or more selection methods according to the present invention and/or one or more other selection methods.

In addition, or in the alternative, the transformed cells selected by the selection method of the present invention can be subsequently subjected to one or more selection methods according to the present invention and/or one or more other selection methods.

The present invention also provides an expression system that enables transformed cells to be selected by the selection method of the present invention. The expression system can be expressing or can be capable of expressing at least the first nucleotide sequence of the present invention. The expression system may be one or more of a vector, construct, plasmid, cell or organism.

If a cell is also to be transformed with a NOI then the expression system will comprise that NOI—which NOI may be present on or in the same vector, construct, plasmid, cell or organism as the first nucleotide sequence. Alternatively the NOI may be present on or in a different vector, construct, plasmid, cell or organism as the first nucleotide sequence. Preferably, the NOI is present on or in the same vector, construct, plasmid, cell or organism as at least the first nucleotide sequence.

If a cell is to be transformed with one or more NOIs and one or more other genes for one or more other selection methods (such as another selection method according to the present invention and/or a known selection method) those other nucleotide sequences may be present on or in the same vector, construct, plasmid, cell or organism as the first nucleotide sequence. Alternatively one or more of those other nucleotide sequences may be present on or in a different vector, construct, plasmid, cell or organism as at least the first nucleotide sequence. Preferably, those other nucleotide sequences are present on or in the same vector, construct, plasmid, cell or organism as the first nucleotide sequence. This allows for workers to easily prepare and easily select for cells that have been transformed with a number of NOIs etc.

In accordance with the present invention there may be a plurality of NOI(s).

The, or each, NOI may be independently selected from DNA or RNA. Preferably, the or each NOI is DNA. More preferably, the or each NOI is recombinant DNA.

As indicated above, the term "recombinant DNA" means DNA prepared by at least one step that utilises at least one recombinant DNA technique.

The term NOI means any desired nucleotide sequence for incorporation into the cells in question to produce genetically transformed cells. Introduction of nucleotide sequences into, for example, plants is widely practised, and it is believed that there are no limitations upon the nucleotide sequences whose presence may be selected (eg. detected) by use of the selection method of the present invention.

By use of the method of the present invention the presence of the NOI in the genetically transformed cells may be determined without the above-mentioned disadvantages associated with the selection systems relying solely on antibiotic resistance and/or herbicide resistance.

The NOI can be any nucleotide sequence of interest, such as any gene of interest. A NOI can be any nucleotide sequence that is either foreign or natural to the cell or organism (e.g. a particular plant) in question. Typical examples of a NOI include genes encoding proteins and enzymes that modify metabolic and catabolic processes. The NOI may code for an agent for introducing or increasing resistance to pathogens. The NOI may even be an antisense construct for modifying the expression of natural transcripts present in the relevant tissues. The NOI may even code for a compound that is of benefit to animals or humans. Examples of NOIs include nucleotide sequences encoding any one or more of pectinases, pectin depolymerases, polygalacturonases, pectate lyases, pectin lyases, rhamnogalacturonases, hemicellulases, endo-α-glucanases, arabinases, or acetyl esterases, or combinations thereof, as well as antisense sequences thereof. The NOI may encode a protein giving nutritional value to a food or crop. Typical examples include plant proteins that can inhibit the formation of anti-nutritive factors and plant proteins that have a more desirable amino acid composition (e.g. a higher lysine content than a non-transgenic plant).

The NOI may even code for an enzyme that can be used in food processing such as chymosin, thaumatin and α-galactosidase. The NOI can be a gene encoding for any one of a pest toxin, an antisense transcript such as that for patatin of-α-amylase, ADP-glucose pyrophosphorylase (e.g. see EP-A-0455316), a protease antisense, a glucanase or genomic β1,4-endoglucanase.

The NOI may even code for or comprise an intron of a particular gene. Here the intron can be in sense or antisense orientation. In the latter instance, the particular gene could be DNA encoding β-1,4-endoglucanase. Antisense expression of genomic exon or intron sequences as the NOI would mean that the natural β-1,4-endoglucanase expression would be reduced or eliminated but wherein the expression of a β-1,4-endoglucanase gene according to the present invention would not be affected.

The NOI may be the nucleotide sequence coding for the arabinofuranosidase enzyme which is the subject of PCT patent application PCT/EP96/01009. The NOI may be any of the nucleotide sequences coding for the ADP-glucose pyrophosphorylase enzymes which are the subject of PCT patent application PCT/EP9401082. The NOI may be any of the nucleotide sequences coding for the c-glucan lyase enzyme which are described in PCT patent application PCT/EP94/03397. The NOI may be any of the nucleotide sequences coding for the glucanase enzyme which are described in PCT patent application PCT/EP96/01008.

The NOI may also encode a permease or other transport factor which allows the compound or precursor thereof or metabolised derivative thereof to cross the cell membrane and enter the transformed cells. Instead of facilitating uptake of a compound into a cell, the co-introduced nucleotide sequence may alternatively direct the component or precursor thereof or metabolised derivative thereof to a specific compartment—such as the plasma membrane or into the vacuole or the endoplasmic reticulum.

More than one NOI can be present.

The NOI can be co-introduced with the first nucleotide sequence according to the present invention.

The term "co-introduced" means that the two nucleotide sequences may be coupled to each other, or are otherwise introduced together, in such a manner that the presence of the co-introduced first nucleotide sequence in a cell indicates that the NOI has been introduced into the cell, i.e. if the first nucleotide sequence is shown to have been introduced, the probability that the NOI has also been introduced is significantly may be introduced by the same vector.

The methods described herein may also be used when the co-introduced first nucleotide sequence and the NOI are introduced independently. This may be performed, for example, by using the same bacteria for incorporation of both genes and incorporating a relatively large number of copies of the NOI into the cells, whereby the probability is relatively high that cells which are shown to express the first nucleotide sequence will also contain and express the NOI.

In order for the introduced first nucleotide sequence and optional NOI to be expressed in the transformed cells, the genetic constructs containing the first nucleotide sequence and/or NOI will typically, but not necessarily, contain regulatory sequences enabling expression of the nucleotide sequences, e.g. known promoters and transcription terminators. Thus, the first nucleotide sequence will typically be associated with a promoter, which may be a constitutive or regulatable promoter, and the NOI will typically also be associated with a constitutive or regulatable promoter.

The term "promoter" is used in the normal sense of the art, e.g. an RNA polymerase binding site in the Jacob-Monod theory of gene expression.

The promoter could additionally include one or more features to ensure or to increase expression in a suitable host. For example, the features can be conserved regions such as a Pribnow Box or a TATA box. The promoters may even contain other sequences to affect (such as to maintain, enhance, decrease) the levels of expression of the nucleotide sequence of the present invention. For example, suitable other sequences include the Shl-intron or an ADH intron. Other sequences include inducible elements—such as temperature, chemical, light or stress inducible elements.

Also, suitable elements to enhance transcription or translation may be present. An example of the latter element is the TMV 5' signal sequence (see Sleat Gene 217 [1987] 217–225; and Dawson Plant Mol. Biol. 23 [1993]97).

The first nucleotide sequence and/or the second nucleotide sequence and/or the third nucleotide sequence and/or the NOI may comprise one or more introns. In particular, if the first nucleotide sequence and/or the second nucleotide sequence and/or the third nucleotide sequence and/or the NOI encodes an expression product that can detrimentally affect a bacterium and all or a part (e.g. a plasmid thereof or therein) of that bacterium is used either to propagate the NOI or as a means to transform the cells, then it may be desirable for that gene product to be inactive in the bacterium. One way of selectively inactivating the gene product in bacteria is to insert one or more introns into the nucleotide sequence of the first nucleotide sequence and/or the second nucleotide sequence and/or the third nucleotide sequence and/or the NOI, respectively. This intron or those introns would not be removed after transcription in the bacterium but would be so removed in, for example, plants etc.

In a highly preferred embodiment, if the first nucleotide sequence and/or the second nucleotide sequence and/or the third nucleotide sequence and/or the NOI comprises at least one intron, then that at least one intron is present in a highly conserved region of the first nucleotide sequence or the NOI.

Here, the term "intron" is used in its normal sense as meaning a nucleotide sequence lying within a coding sequence but being removable therefrom.

As mentioned above, the method of the present invention is particularly suitable for the selection of genetically transformed plant cells, thereby allowing identification and isolation of such cells without being essentially dependent on the use of selection genes coding for antibiotic or herbicide resistance.

The selection method of the present invention may be used for selecting cells in vitro. However, the selection method of the present invention may also be employed in vivo in the sense that it is possible to selectively grow transformed organisms—such as plants—from cells, tissues etc. that comprise the selection system of the present invention.

In vivo use of the selection method of the present invention is of particular importance in connection with genetic transformation performed on whole plants or on plant parts, in which the plants or plant parts comprise both transformed and non-transformed cells, since selection of the transformed cells can, in some instances, be achieved without directly damaging the neighbouring non-transformed cells. For example, in some instances, the transformed cells have a selective advantage compared to the non-transformed cells—such as the ability to still form shoots—but the non-transformed cells suffer in the sense of being damaged or killed, as is the case with using antibiotics or herbicides.

In certain cases, such as when an improved selection frequency is desired, it may be advantageous for the cells to be transformed with a nucleotide sequence that is a selection gene different to the first nucleotide sequence. This additional, selection nucleotide sequence may be an additional gene coding for an enzyme (or other protein or polypeptide) suitable for selection according to the present invention, or it may be a gene coding for an enzyme (or other protein or polypeptide) for a known selection method, eg coding for resistance to a antibiotic or herbicide or it may be a gene suitable for selection by the selection methods described in WO 93/05163 and/or WO 94/20627. Thus, genetically transformed cells may be selected using a combination of selection techniques. For example, if the transformed cells also possessed genes coding for resistance to at least one antibiotic or herbicide, then the medium could additionally comprise at least one antibiotic or herbicide to which the transformed cells are resistant. In particular, we have found that the medium of the present invention does not impair the effectiveness of the known selection methods that rely on herbicide or antibiotic resistance.

The selective advantage possessed by the transformed cells of the present invention may be any difference or advantage with regard to the non-transformed cells which allows the transformed cells to be readily identified and isolated from the non-transformed cells. This may, for example, be a difference or advantage allowing the transformed cells to be identified by simple visual means, i.e. without the use of a separate assay to determine the presence of a gene that provides the selection means.

As mentioned above, one aspect of the present invention relates to genetically transformed cells which have been selected according to the above method, in particular plant cells, as well as plants, progeny or seeds derived from or derivable from such genetically transformed plant cells. In particular, it is often an advantage that these cells are genetically transformed plant cells whose genome does not contain an introduced (i.e. non-native) nucleotide sequence coding for toxin-resistance, antibiotic-resistance or herbicide-resistance as a selection means. As explained above, there are concerns about whether it is safe to incorporate genes coding for eg antibiotic resistance in eg food plants. Genetically transformed plant cells selected by the method of the present invention which do not contain selection genes for eg antibiotic resistance, as well as plants, progeny and seeds derived from such cells, are therefore clearly advantageous in this respect.

The transformed cells may be prepared by techniques known in the art. For example, if the transformed cells are transformed plant cells reference may be made to EP-B-0470145 and CA-A-2006454.

Even though the selection method according to the present invention is not disclosed in EP-B-0470145 and CA-A-2006454, those two documents do provide some useful background commentary on the types of techniques that may be employed to prepare the transformed plant cells and transgenic plants according to the present invention. Some of these background teachings are now included in the following commentary.

The basic principle in the construction of genetically modified plants is to insert genetic information in the plant genome so as to obtain a stable maintenance of the inserted genetic material.

Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech Mar./Apr. 1994 17–27).

Thus, in one aspect, the present invention relates to a vector system which carries a first nucleotide sequence or construct according to the present invention and which is capable of introducing the nucleotide sequence or construct into the genome of an organism, such as a plant.

The vector system may comprise one vector, but it can comprise at least two vectors. In the case of two vectors, the vector system is normally referred to as a binary vector system. Binary vector systems are described in further detail in Gynheung A n et al. (1980), Binary Vectors, *Plant Molecular Biology Manual A*3, 1–19.

One extensively employed system for transformation of plant cells with a given promoter or nucleotide sequence or construct is based on the use of a Ti plasmid from *Agrobacterium tumefaciens* or a Ri plasmid from *Agrobacterium rhizogenes* (An et al. (1986), *Plant Physiol.* 81, 301–305 and Butcher D. N. et al. (1980), *Tissue Culture Methods for Plant Pathologists*, eds.: D. S. Ingrams and J. P. Helgeson: 203–208).

Several different Ti and Ri plasmids have been constructed which are suitable for the construction of the plant or plant cell constructs described above.

The first nucleotide sequence or construct of the present invention should preferably be inserted into the Ti-plasmid between the border sequences of the T-DNA or adjacent a T-DNA sequence so as to avoid disruption of the sequences immediately surrounding the T-DNA borders, as at least one of these regions appear to be essential for insertion of modified T-DNA into the plant genome.

As will be understood from the above explanation, if the organism is a plant, then the vector system of the present invention is preferably one which contains the sequences necessary to infect the plant (e.g. the vir region) and at least one border part of a T-DNA sequence, the border part being located on the same vector as the genetic construct.

Preferably, the vector system is an *Agrobacterium lumefaciens* Ti-plasmid or an *Agrobacterium rhizogenes* Ri-plasmid or a derivative thereof, as these plasmids are well-known and widely employed in the construction of transgenic plants, many vector systems exist which are based on these plasmids or derivatives thereof.

In the construction of a transgenic plant the promoter or nucleotide sequence or construct of the present invention may be first constructed in a microorganism in which the vector can replicate and which is easy to manipulate before insertion into the plant. An example of a useful microorganism is *E. coli.*, but other microorganisms having the above properties may be used. When a vector of a vector system as defined above has been constructed in *E. coli.* it is transferred, if necessary, into a suitable *Agrobacterium* strain, e.g. *Agrobacterium tumefaciens*. The Ti-plasmid harbouring the first nucleotide sequence or construct of the invention is thus preferably transferred into a suitable *Agrobacterium* strain, e.g. *A. tumefaciens*, so as to obtain an *Agrobacterium* cell harbouring the promoter or nucleotide sequence or construct of the invention, which DNA is subsequently transferred into the plant cell to be modified.

Naturally, the present invention is not limited to just the use of *Agrobacterium* systems to transform plants. In this regard, other suitable techniques may be used—such as electroporation and/or particle bombardment (biolistics).

As reported in CA-A-2006454, a large number of cloning vectors are available which contain a replication system in *E. coli* and a selection means which allows a selection of the transformed cells. The vectors contain for example pBR322, the pUC series, the M13 mp series, pACYC 184 etc. In this way, the promoter or nucleotide or construct of the present invention can be introduced into a suitable restriction position in the vector. The contained plasmid is used for the transformation in *E. coli*. The *E. coli* cells are cultivated in a suitable nutrient medium and then harvested and lysed. The plasmid is then recovered and then analysed—such as by any one or more of the following techniques: sequence analysis, restriction analysis, electrophoresis and further biochemical-molecular biological methods. After each manipulation, the used DNA sequence can be restricted or selectively amplified by PCR techniques and connected with the next DNA sequence. Each sequence can be cloned in the same or different plasmid.

After each introduction method of the first nucleotide sequence or construct according to the present invention in the plants the presence and/or insertion of further DNA sequences may be necessary. If, for example, for the transformation the Ti- or Ri-plasmid of the plant cells is used, at least the right boundary and often however the right and the left boundary of the Ti- and Ri-plasmid T-DNA, as flanking areas of the introduced genes, can be connected. The use of T-DNA for the transformation of plant cells has been intensively studied and is described in EP-A-120516; Hoekema, in: The Binary Plant Vector System Offset-drukkerij Kanters B. B., Alblasserdam, 1985, Chapter V; Fraley, et al., Crit. Rev. Plant Sci., 4:1–46; and An et al., EMBO J. (1985) 4:277–284.

Direct infection of plant tissues by *Agrobacterium* is a simple technique which has been widely employed and which is described in Butcher D. N. et al. (1980), *Tissue Culture Methods for Plant Pathologists*, eds.: D. S. Ingrams and J. P. Helgeson, 203–208. For further teachings on this topic see Potrykus (Annu Rev Plant Physiol Plant Mol Biol [1991]42:205–225) and Christou (Agro-Food-Industry Hi-Tech Mar./Apr. 1994 17–27). With this technique, infection of a plant may be done on a certain part or tissue of the plant, i.e. on a part of a leaf, a root, a stem or another part of the plant.

Typically, with direct infection of plant tissues by *Agrobacterium* carrying the first nucleotide sequence or the construct, a plant to be infected is wounded, e.g. by cutting the plant with a razor or puncturing the plant with a needle or rubbing the plant with an abrasive. The wound is then inoculated with the *Agrobacterium*. The inoculated plant or plant part is then grown on a suitable culture medium.

When plant cells are constructed, these cells are grown and, optionally, maintained in a medium according to the present invention following well-known tissue culturing methods—such as by culturing the cells in a suitable culture medium supplied with the necessary growth factors such as amino acids, plant hormones, vitamins, etc, but wherein the culture medium comprises a component according to the present invention. Regeneration of the transformed cells into genetically modified plants may be accomplished using known methods for the regeneration of plants from cell or tissue cultures, for example by selecting the transformed shoots and by subculturing the shoots on a medium containing the appropriate nutrients, plant hormones, etc.

Further teachings on plant transformation may be found in EP-A-0449375.

Reference may even be made to Sprngstad et al (1995 Plant Cell Tissue Organ Culture 40 pp 1–15) as these authors present a general overview on transgenic plant construction.

In a highly preferred embodiment, the present invention is based on our finding that it is possible to use constructs comprising an expressable nucleotide sequence gene coding for any one or more of galactokinase (EC 2.7.1.6), UTP-dependent pyrophosphorylase (EC 2.7.7.10), UDP-glucose-dependent uridylyltransferase (EC 2.7.7.12), UDP-galactose epimerase (EC 5.1.3.2) to prepare transformed cells wherein the transformed cells can be selected from non-transformed cells.

In addition, the present invention also covers transgenic plants comprising the transformed cells or constructs of the present invention.

Thus, in a highly preferred embodiment the present invention covers transgenic plants comprising transformed cells or constructs that comprise an expressable nucleotide sequence gene coding for any one or more of galactokinase (EC 2.7.1.6), UTP-dependent pyrophosphorylase (EC 2.7.7.10), UDP-glucose-dependent uridylyltransferase (EC 2.7.7.12), UDP-galactose epimerase (EC 5.1.3.2).

In order to explain in more detail these highly preferred aspects of the present invention, reference shall be made to at least FIGS. 1–2, in which FIG. 1 is a schematic diagram of a metabolic pathway;

FIG. 2 is a schematic diagram of a metabolic pathway.

Galactose metabolism in plants have been studied in Petunia which is one of the very few plant species being able to use galactose as carbon source to sustain growth (Dressier et al. 1982). The first step of galactose metabolism in Petunia as well as in yeast and other microorganisms is the phosphorylation of galactose to galactose-1-phosphate by galactokinase (EC 2.7.1.6) (see FIGS. 1 and 2 below). The next step is the conversion to UDP-galactose which in Petunia can be performed by either a UTP-dependent pyrophosphorylase (EC 2.7.7.10) or a UDP-glucose-dependent uridylyltransferase (EC 2.7.7.12) while in microogansims only or predominantly the latter reaction occurs. The UDP-galactose is finally converted to UDP-glucose by UDP-galactose epimerase (EC 5.1.3.2). Thus, the conversion of galactose to a glucose-containing metabolite is irreversible.

The reason for the toxicity of galactose on plant cells is believed to be due to the absence of one or more of the enzymatic activities required for the conversion of galactose to UDP-glucose. Thus, in order to use galactose as selective agent, the transformed plant cells must be supplemented with the lacking gene(s) so that enzymatic activities for the entire pathway from galactose to UDP-glucose are present.

However, it is likely that many plant species do not require the insertion of all 3 genes in the Leloir pathway as the absence of just one gene in this pathway will render the plant tissue sensitive to galactose.

The first enzyme in galactose metabolism is galactokinase which has been reported to be present in some plants such as Vicia faba (Dey 1983), *Phaseolus areus* (Chan and Hassid 1975; Neufeld et at. 1960), barley and corn (Roberts et al. 1971). Roberts et al. (1971) studied the accumulation of galactose containing metabolites in corn roots fed with toxic levels of galactose and they found that free galactose and galactose-1-phosphate each accounted for close to 50% of the indentifiable metabolites. These data were in accordance with the hypothesis that the causal agent of galactose toxicity may be galactose-1-phosphate. As galactose is toxic to most plant species, this in turn implies that many plant species have galactokinase activity.

The next enzyme in the galactose metabolism is UTP-hexose-1-phosphate uridyltransferase or UDP-glucose uridylyltransferase. Both of these enzymes—which are rare—may be found in Petunia.

In contrast to the two preceeding enzymes, the last enzyme, UDP-galactose epimerase, has been reported in a range of plant species such as fenugreek (Clermont and Percheron 1979), wheat (Fan and Feingold 1969), sugarcane (Maretzki and Thom 1978) and various trees (Dalessandro and Northcote 1977) in addition to the above mentioned species. The reason for the widespread occurrence of this enzyme is presumably related to the fact that its main function is the production of UDP-galactose from UDP-glucose for the synthesis of cell wall components.

Thus, in order to enable transformed plant tissue to metabolise galactose, it is likely that it is sufficient for some plant species to introduce just one gene eg. a UTP-hexose-1-phosphate transferase gene or a UDP-glucose uridylyl-transferase gene which would then function as the selectable gene. However, for other plant species it may be required to introduce two or even three genes involved in the metabolism of galactose. From a technical point of view, it presents no problems to use more than one gene as selectable gene.

Although a galactose selection system also employs a carbohydrate as selective agent, it does not resemble 'positive selection' due to the high toxic effect of galactose.

The selection system described here is based on enabling transformed plant cells to metabolise D-galactose. This D-galactose can be supplied to the plant cells or tissues during selection as free D-galactose or as a D-galactose containing compound. Examples of such D-galactose containing compounds are α-lactose (β-D-galactopyranosyl [1→4]-α-D-glucose, milk sugar), β-lactose, melibiose (6-O-α-D-galacto-pyranosyl-D-glucose), raffinose, stachyose, verbascose and galactinol which all liberate free D-galactose upon hydrolysis by either α-galactosidases or β-galactosidases which are present in a wide range a plant species and tissues.

Other examples of potentially useful compounds for galactose selection are chemically derivatized D-galactose such as D-galactose pentaacetate and methyl galactoside, from which free D-galactose can be produced by the action of appropriate enzymes present in plant cells.

It can also be envisaged that the galactose selection system can be modified so that galactose-1-phosphate can be used as selective agent, in which case the selectable gene is most likely to be an UTP-hexose-1-phosphate uridyltransferase gene or an UDP-glucose uridylyltransferase gene.

Yet another modification of the galactose selection system relates to the addition of other carbohydrates or other substances to the selection medium which affect the toxicity of galactose. Furthermore it will also be obvious for those skilled in the art that changes in the employed galactose concentration in the course of the selection can affect selection efficiency.

Thus, the present invention provides a new selection method based on the novel use of galactose and/or a derivative thereof and/or a precursor thereof.

As galactose and the genes encoding the enzymes responsible for the metabolism of galactose are well-characterized, we believe that galactose would be suitable for use as a selective agent for the selection of transgenic cells, tissues, organs, organisms (such as plants), provided that the transgenic cells, tissues, organs, organisms (such as plants) aquire the appropiate genes for metabolising, detoxifying and/or tolerating galactose.

The present invention will now be described only by way of examples in which reference is made to the following Figures:

FIG. 3 is presents sequence information; and
FIG. 4 is a schematic diagram of a plasmid.

In more detail. FIG. 3 is the complete nucleotide sequence (SEQ. ID. NO. 1) of the *E. coli* galT gene with the deduced amino acid sequence (SEQ. ID. NO. 2) shown below the nucleotide sequence. The primers used for the isolation of the gene by PCR are shown with arrows indicating the 5' to 3' direction.

In more detail, FIG. 4 is a plasmid map of the plant transformation vector pVIC-GalT.

Transformation Studies

The following examples demonstrate that the genes coding for galactokinase (EC 2.7.1.6) (galK), UTP-dependent pyrophosphorylase (EC 2.7.7.10) (galP), UDP-glucose-dependent uridyl transferase (EC 2.7.7.12) (galT), UDP-galactose epimerase (EC 5.1.3.2) (galE) gene can be used as a means to provide selection of transformed cells, such as transgenic potato or maize shoots, on or in media containing galactose or a derivative thereof as a selective agent. For convenience, the term galX has been used to denote any one or more of galK, galP, galT, galE.

EXAMPLE 1

Transgenic Potato Plants

General teachings on potato transformation may be found in our copending patent applications PCT/EP96103053, PCT/EP96/03052 and PCT/EP94/01082 (the contents of each of which are incorporated herein by reference).

For the present studies, the following protocol was adopted.

Plasmid Construction

The disarmed *Agrobacterium tumefaciens* strain LBA 4404, containing the helper vir plasmid pRALA4404 (Hoekema et al, 1983 Nature 303 pp 179–180), was cultured on YMB agar ($K_2HPO_4.3H_2O$ 660 mg $l^{-1}$, $MgSO_4$ 200 mg $l^{-1}$, NaCl 100 mg $l^{-1}$, mannitol 10 g $l^{-1}$, yeast extract 400 mg $l^{-1}$, 0.8% w/v agar, pH 7.0) containing 100 mg $l^{-1}$ rifampicin and 500 mg $l^{-1}$ streptomycin sulphate. Transformation with a plasmid containing galX under the control of a plant expressable promoter (such as the E35S promoter) was accomplished using the freeze-thaw method of Holters et al (1978 Mol Gen Genet 163 181–187) and transformants were selected on YMB agar containing 100 mg $l^{-1}$ rifampicin and 500 mg l$^{-1}$ streptomycin, and 50 mg l$^{-1}$ gentamycin sulphate. The resultant plasmid is called pVICTOR IV 35S galX. Transformation with a control construct lacking the galX gene was performed in the same manner. In addition, the T-DNA will include a screenable marker gene encoding a screenable marker enzyme, such as the β-glucuronidase gene from *E. coli*, driven by a plant expressable promoter. This facilitates the optimization of the methods as transgenic cells/shoots/plants are more easily found using this marker (Jefferson et al 1987, EMBO J, 6:3901–3907).

Transformation of Plants

Shoot cultures of *Solanum tuberosum cv Saturna* were maintained on LS agar containing Murashige Skoog basal salts (Sigma M6899) (Murashige and Skoog (1965) Physiol. Plant. 15: 473–497) with 2 μM silver thiosulphate, and nutrients and vitamins as described by Linsmaier and Skoog (1965 Physiol. Plant. 18 100–127). Cultures were maintained at 25° C. with a 16 h daily photoperiod. After approximately 40 days, subculturing was performed and the shoots cut into segments of approximately 8 mm length.

Shoot cultures of approximately 40 days maturity (5–6 cm height) were cut into 8 mm internodal segments and/or leaves were cut off and wounded by making 24 small cuts over the midrib of the leaf. These were then placed into liquid LS-medium containing *Agrobacterium rumefaciens* transformed with pVICTOR IV 35S galX ($A_{660}$=0.5, pathlength 1 cm). Following incubation at room temperature for 30 minutes, the segments were dried by blotting on to sterile filter paper and transferred to LS agar (0.8% w/v containing 2 mg l$^{-1}$ 2,4-dichlorophenoxyacetic acid and 500 μg l$^{-1}$ trans-zeatin. The explants were covered with filter paper, moistened with LS medium, and covered with a cloth for three days at 25° C. Following this treatment, the segments can be washed with liquid LS medium containing 800 mg l$^{-1}$ carbenicillin, and then transferred on to LS agar (0.8% w/v) containing 1 mg l$^{-1}$ trans-zeatin, 100 mg l$^{-1}$ gibberellic acid (GA3), with sucrose (eg 10–20 g l$^{-1}$). This agar contains galactose (eg such as in an amount of from about 0.5–5.0 g l$^{-1}$).

The segments were sub-cultured to fresh substrate each 3–4 weeks. In 3 to 4 weeks, shoots develop from the segments and the formation of new shoots continued for 3–4 months.

The regenerated shoots are maintained on substrate composed of LS-substrate, 0.002 mM silver thiosulphate and agar (8.0 g/l). Carbenicillin (800 mg/l) can be added if desired.

The transgenic plants may be verified by performing a β-glucuronidase assay on the leaf tips of the surviving shoots according to Hodal et al. (Plant. Sci. (1992), 87: 115–122).

Alternatively, the transgenic genotype of the regenerated shoot may be verified by performing NPTII assays (Radke, S. E. et al, *Theor. Appl. Genet.* (1988), 75: 685–694) or by performing PCR analysis according to Wang et al (1993, NAR 21: 4153–4154).

The shoots (height approximately 2–3 cms) were transplanted from rooting substrate to soil and placed in a growth chamber (21° C., 16 hour light 200–400 μE/m²/sec).

When the plants were well established they were transferred to the greenhouse, where they were grown until tubers had developed and the upper part of the plants were senescing.

Harvesting

The potatoes were harvested after about 3–6 months and then analysed.

The transformed shoots can be distinguished from the non-transformed shoots by adding galactose to their substrate of leaf tips cultured in in-vitro. After harvest of the shoots, the transformed shoots can be selected by adding amounts of galactose to the shoot medium. The transformed shoots will be resistent to galactose and will survive as opposed the non-transformed shoots which will be inhibited in growth.

Analysis of Transformants

In order to confirm the integration of galX, genomic DNA may be isolated by the method of Dellaporta er al (1983 Plant Mol Biol Rep 1 19–21) and samples of this DNA, digested with EcoRI, subjected to electrophoresis in an 0.8% w/v agarose gel and transferred to Hybond N+ membranes (Amersham) by Southern blotting (Southern, 1975 J Mol Biol 98 503–517). Probes for the coding region of galX may be used as templates for random primed synthesis of $^{32}$P-labelled probe after the method of Feinberg and Vogelstein (1983 Anal Bioch 137 266–267) and hybridised to the Southern blots at high stringency (65° C., 0.1×SSC).

Selection of transgenic shoots was accomplished using a selection medium according to the present invention.

Transgenic shoots are obtained on selection media according to the present invention indicating that the selection medium can be varied significantly and remain useful for the selection of transgenic shoots.

EXAMPLE 2

Transgenic Maze Plants

Introduction

Since the first publication of production of transgenic plants in 1983 (Leemans, 1993 Biotechnology 11 s22), there have been numerous publications of production of transgenic plants including especially dicotyledon crop plants.

Until very recently there were very few reports on successful production of transgenic monocotyledononary crop plants. This relatively slow development within monocots were due to two causes. Firstly, until the early 1980s, efficient regeneration of plants from cultured cells and tissues of monocots had proven very difficult. This problem was ultimately solved by the culture of explants from immature and embryogenic tissue, which retain their morphogenic potential on nutrient media containing plant growth regulators. Secondly, the monocots are not a natural host for *Agrobacterium tumefaciens*, meaning that the successful developed techniques within the dicots using their natural vector *Agrobacterium tumefaciens* was unsuccessful for many years in the monocots.

Nevertheless, it is now possible to successfully transformation and produce fertile transgenic plants of maize using methods such as: (1) Silicon Carbide Whiskers; (2) Particle Bombardment; (3) DNA Uptake by PEG treated protoplast; or (4) DNA Uptake in Electroporation of Tissue. Each of these methods—which are reviewed by Thompson (1995 Euphtytica 85 pp 75–80)—may be used to prepare inter alia transgenic maize according to the present invention.

In particular, the particle Gun method has been successfully used for the transformation of monocots. However, EP-A-0604662 reports on a different method of transforming monocotyledons. The method comprises transforming cultured tissues of a monocotyledon under or after dedifferentiation with *Agrobacterium* containing a super binary vector as a selection means a hygromycin-resistant gene was used. Production of transgenic calli and plant was demonstrated using the hygromycin selection. This method may be used to prepare inter alia transgenic maize according to the present invention.

Subsequent to the method of EP-A-0604662, EP-A-0672752 reports on non-dedifferentiated immature embryos. In this regard, both hygromycin-resistance and PPT-resistance genes were used as the selection means, with PPT giving rise to 10% or more independent transformed plants.

This method may be used to prepare inter alia transgenic maize according to the present invention.

To date, it would appear that transgenic maize plants can be successfully produced from easily-culturable varieties—such as the inbred line A188. In this regard, see the teachings of Ishida et al (1996 Nature Biotechnology 14 pp 745–750). The method disclosed by these workers may be used to prepare inter alia transgenic maize according to the present invention.

Vasil (1996 Nature Biotechnology 14 pp 702–703) presents a further review article on transformation of maize.

Even though it is possible to prepare transformed maize by use of, for example, particle Gun mediated transformation, for the present studies the following protocol is adopted.

Plasmid Construction

The same protocol as outlined above is adopted. In this respect, the protocol also uses pVICTOR IV 35S galX. Likewise, transformation with a control construct lacking the galX gene was performed in the same manner.

Isolation and Cocultivation of Explants

Immature embryos of, for example, maize line A188 of the size between 1.5 to 2.5 mm were isolated and cocultivated with *Agrobacterium tumefaciens* strain LBA 4404 in N6-AS for 2–3 days at 25° C. under illumination. Thereafter, the embryos were washed with sterilized water containing 250 mg/l of cefotaxime and transferred to an LS medium and 250 mg/l cefotaxime and galactose in concentrations of up to 100 mg/l (the medium is hereafter called LSS2).

Conditions for the Selection of Transgenic Plants

The explants were cultured for three weeks on LSS2 medium and then transferred to an LS medium containing galactose and optionally cefotaxime. After three weeks on this medium, green shoots were isolated and tested for β-glucuronidase (Jefferson et al 1987, EMBO J 6:3901–3907) activity.

Rooting of β-glucronidase Positive Shoots

β-glucuronidase positive shoots were transferred to an MS medium containing 2 mg/l for rooting. After four weeks on this medium, plantlets are transferred to pots with sterile soil for acclimatisation.

Selection of transgenic shoots was accomplished using a selection medium accoding to the present invention.

After four weeks the shoots were harvested and all explants were transferred to fresh selection medium (same composition) and after another four weeks of selection the last shoots were harvested.

After harvest, the shoots were analysed for GUS activity using the histochemical assay.

Transgenic shoots are obtained on selection media according to the present invention indicating that the selection medium can be varied significantly and remain useful for the selection of transgenic shoots.

EXAMPLE 3

Toxicity of Galactose to Various Plant Species

In order to be useful for selection, the selective component (otherwise called selective agent) should not be able to sustain significant growth and preferably have adverse/toxic effects to the non-transformed cells/tissues. To assess the applicability of galactose selection following transformation, a number of plant species representing a range of different botanical families were tested for sensitivity to galactose, using explants which may be suitable for transformation experiments.

Galactose was unable to sustain growth of any of the tested plant species (wheat, sunflower, oil seed rape, potato, sugar beet, pea and Petunia) with varying levels of toxicity. The only fairly tolerant species was Petunia, in accordance with expectations as Petunia has been reported to have all necessary enzymatic activities for metabolising galactose (Dressier et al. 1982. *Z. Pflanzenphysiol.* 107: 409–418).

3.1. Wheat (*Triticum aestivum*)

As an example of a monocotyledonous species, wheat was studied. Immature wheat embryos (2–3 weeks old, a total of 161) were carefully removed from the seed and were cultivated on Gamborg B5 medium (Gamborg et al. 1968. Exp. Cell Res. 50: 151–158) supplemented with 9.0 g/l Bacto agar. 20 g/l sucrose and galactose according to the experiment. The embryos were cultivated in the dark for about 10 days where germinated embryos were transferred to fresh medium of the same composition and cultivated in a 16 h/8 h day/night regime for 4–5 weeks. The effect of galactose was evaluated by the number of germinated embryos and by measuring the length of the leaf on these embryos, relative to the control medium (no galactose).

|  | Galactose concentration (g/l) | | | | | |
| --- | --- | --- | --- | --- | --- | --- |
|  | 0 | 2.5 | 5.0 | 7.5 | 10 | 15 |
| Germination of embryos | 100 | 43 | 29 | 0 | 14 | 0 |
| Average shoot length | 100 | 89 | 67 | 0 | 33 | 0 |

The data in the above table clearly demonstrate that galactose has a strong inhibiting effect on the immature embryos as both germination and growth of the shoots were significantly reduced. The galactose selection method of the present invention can be used for the production of transgenic wheat.

Roberts et al. (1981. Plant Physiol. 48: 36–42) found that galactose was toxic to tissues of maize (*Zea maize*) and of barley (*Hordeum vulgare*). This indicates that the galactose selection method of the present invention may also be usefull for the selection of transgenic shoots of these species.

3.2 Sunflower (*Helianthus annuus*)

The preparation of apical explants useful for the transformation of sunflower were modified according to Knittel et al. (1994. Plant Cell Rep. 14: 81–86). The seed coats of 2 d old seedlings were gently removed and the cotyledons, the emerging root and the top of the apex were removed. The remaining part of the apex was cut off and divided into two halves and cultivated according to Knittel et al., with 20 g/l sucrose in the medium and galactose according to the experiment. After 4–5 weeks of culture at a 16 h/8 h day/night regime, growth was monitored by determining the fresh weight of the explants (above controls grown on a medium devoid of any carbohydrate source).

|  | Galactose concentration (g/l) | | | | |
| --- | --- | --- | --- | --- | --- |
|  | 0 | 5.0 | 7.5 | 10 | 15 |
| Fresh weight (mg/explant) | 144 | 28 | 0 | 0 | 0 |

The data show that galactose is toxic to sunflower explants. The data indicate that the galactose selection method of the present invention may be employed successfully for the selection of transgenic sunflower shoots.

3.3. Oil Seed Rape (*Brassica napus*)

Hypocotyl explants useful for the transformation of oil seed rape were prepared using a protocol modified after Radke et al. (1988. Theor. Appl. Genet. 78: 161–168). Hypocotyls of 5 d old seedlings were cut into 1 cm segments and transferred to modified MS-medium (Murashige and Skoog 1962. Physiol. Plant. 15: 473–497) containing sucrose and galactose according to the experiment. After 3–4 weeks, shoots were harvested and the explants were transferred to fresh medium of the same composition. This was repeated for 3 more harvests and the total number of regenerated shoots formed on each medium was calculated (see table below).

|  | Sucrose concentration (g/l) | | | |
| --- | --- | --- | --- | --- |
|  | 0 | 5.0 | 10 | 20 |
| 0 g/l galactose | 0 | — | — | 60 |
| 2.5 g/l galactose | 0 | 1 | 7 | 26 |
| 5.0 g/l galactose | 0 | 0 | 3 | 22 |

The data in the above Table clearly show that galactose is toxic to oil seed rape. Hence, the data indicate that the galactose selection method of the present invention may be used for the selection of transgenic shoots of oil seed rape and presumably related species. It is expected that higher concentrations of galactose are even more toxic.

The data also demonstrate that the toxic effect of galactose strongly interacts with sucrose as increasing concentrations of sucrose progressively reduces the toxic effect of galactose. Hence, for some applications, preferably galactose is present in low amounts of sucrose.

3.4. Potato (*Solanum ruberosum*)

Young leaves useful for the transformation of potato were prepared from leaves of 28 d old in vitro shoot cultures. The leaves were cut off avoiding the meristem at the leaf corner and were cut twice across the midvein. The explants were then put on modified MS-medium (Murashige and Skoog 1962. Physiol. Plant. 15: 473–497) containing various concentrations of sucrose and galactose. After 3 weeks, shoots were harvested and the explants were transferred to fresh medium of the same composition. This was repeated for 2 more harvests and the total number of explants with regenerated shoots formed on each medium was calculated (see table below).

|  | Sucrose concentration (g/l) | | | | |
| --- | --- | --- | --- | --- | --- |
|  | 0 | 5.0 | 10 | 20 | 30 |
| 0 g/l galactose | 0 | — | — | — | 14 |
| 2.5 g/l galactose | 1 | 0 | 0 | 7 | — |
| 5.0 g/l galactose | 0 | 0 | 0 | 0 | — |

The data in the above Table clearly show that galactose is toxic to potato. The data indicate that the galactose selection method of the present invention may be used for the selection of transgenic shoots of potato and presumably related species. Like oil seed rape, these data also demonstrate that the toxic effect of galactose strongly interacts with sucrose as increasing concentrations of sucrose progressively reduces the toxic effect of galactose. We believe that such interaction is likely to take place also for many other plant species. We also believe that such interaction will also be observed with other carbohydrates than sucrose, such as glucose, fructose and maltose etc. Hence, for some applications, preferably galactose is present in low amounts of carbohydrate (i.e. in amounts that do not affect substantially the effect of the galactose).

3.5. Sugar Beet (*Beta vulgaris*)

Cotyledonary explants useful for the transformation of sugar beet were prepared by excising the cotyledons from 34 weeks old seedlings (Joersbo er al. 1998. Mol. Breeding 4: 111–117). The leaves were transferred to modified MS-medium (Murashiee and Skoog 1962. Physiol. Plant. 15: 473–497) containing 20 g/l sucrose and various concentrations galactose.

After 4–5 weeks, the number of shoots and the fresh weight of the explants were determined and a significant reduction of both growth parameters was observed. The data indicate that the galactose selection method of the present invention may be used for the selection of transgenic shoots of sugar beet and presumably related species.

3.6. Pea (*Pisum sativum*)

Hypocotyl explants useful for the transformation of pea were prepared by excising the hypocotyl from 7 d old seedlings and transferred to a medium, according to Nielsen er al. (1991. Physiol. Plant 82: 99–102), containing various concentrations of sucrose and galactose. After 5 weeks, the growth of the explants were evaluated. The results showed that galactose was unable to sustain any growth of the explants, as opposed to the control medium containing 20 g/l sucrose (no galactose) where the explants produced a manyfold increased fresh weight. The data indicate that the galactose selection method of the present invention may be used for the selection of transgenic shoots of pea and presumably related species.

EXAMPLE 4

Galactose Selection Employed for the Selection of Transgenic Shoots

Introduction

In one preferred embodiment, it is desirable to use up to 3 genes encoding enzymes useful for the conversion of galactose to UDP-glucose. However, in some instances we have found that only one gene may be used. An example of such a gene is that coding for a UTP-dependent pyrophosphorylase (EC 2.7.7.10) or a UDP-glucose-dependent uridyl transferase (EC 2.7.7.12). In some instances, these individual genes may be sufficient for the selection of transgenic shoots of many plant species because both galactokinase (EC 2.7.1.6) and UDP-galactose epimerase (EC 5.1.3.2) occur naturally in many plant species.

In this example, a further example (i.e. in addition to Example 1) the successful selection of transgenic potato shoots is described. These particular experiments used a transformation vector including an *E. coli* gene (galT) encoding UDP-glucose-dependent uridyl transferase (EC 2.7.7.12).

The fact that it was possible select transgenic potato shoots on galactose containing media is in accordance with the toxicological test where potato was found to be sensitive to galactose. Consequently, it is expected that transgenic shoots of other plant species that are sensitive to galactose also can be selected using galactose selection.

4.1. Transformation Vector

An *E. coli* galT gene encoding galactose-1-phosphate uridyltransferase has been cloned, sequenced and introduced into a plant transformation vector. The cloned gene consists of 1060 base pairs and codes for a 348 amino acid protein. Transformation of a galT deficient *E. coli* strain resulted in colonies able to grow on galactose as sole carbon source, indicating that the cloned gene expresses a functional enzyme capable of complementing the galT deficiency. The gene was furnished with an enhanced 35S promoter and a 35S terminator and inserted into a plant transformation vector based on our pVIC vector, into which a GUS gene was also inserted.

Cloning and Characterization of the *E. coli* galT Gene.

The galT gene of *E. coli* was isolated and cloned by PCR from genomic DNA isolated from an *E. coli* strain that can metabolise galactose. The galT gene was found in the GenBank Sequence Database, and the nucleotide sequence was used to design PCR primers for the amplification of the coding region of the gene. To facilitate cloning into our expression vectors the upstream primer was designed such that a PstI site was added to the 5' end of the primer, and the downstream primer was similarly designed with a SalI site. A 1050 base pair DNA fragment obtained after PCR was cloned into the TA cloning vector pCR 2.1-TOPO. Five of the clones were completely sequenced and one clone was selected for further use. The nucleotide sequence of the selected clone (FIG. 3) was identical to that of Cornwell et al. (1987. Nucl. Acids Res. 15: 8116). Translation of the cloned galT gene revealed an open reading frame of 1047 base pairs encoding a 348 amino acid protein (FIG. 3) in agreement with the published sequence (Cornwell et al. 1987. Nucl. Acids Res. 15: 8116).

Construction of a Plant Transformation Vector with the galT Gene

A plant transformation vector called pVIC for *Agrobacterium* mediated transformation was used. pVIC contains the following features: Right- and left border sequences (RB and LB) are from the *A.tumefaciens* plasmid pTiT37 (Yadav et al. 1982. Proc. Natl. Acad. Sci. 79: 6322–6326). The replication origin (pUC Ori) for replication and maintenance in *E. coli* is from the plasmid pUC19 (Yanish-Perron et al. 1985. Gene 33: 103–119). The replication origin (PVSI Ori) for replication and maintenance in *A.tumefaciens* is from the *Pseudomonas* plasmid pVS1 (Itoh et al. 1984. Plasmid 11: 206–220). The bacterial spectinomycin/streptomycin resistance gene (Spec/Strep) is from the transposon Tn7 (Fling et al. 1985. Nucl. Acids Res. 19: 7095–7106) and is fused to the hybrid trp-lac promoter (Amman et al. 1983. Gene 25: 167–178) for efficient bacterial expression. A β-glucuronidase gene (Jefferson et al. 1986. Proc. Natl. Acad. Sci.83: 8447–8451) containing an intron of the ST-LSI gene from potato, preventing expression in bacteria (Vancanneyt et al. 1990. Mol. Gen. Genet. 220: 245–250) was furnished with a $^{35}$S promoter and a $^{35}$S terminator and was introduced into pVIC. This construct was used as a vector for the galt gene. The cloned galT gene was cloned between an enhanced 35S promoter (E35S PR) and the 35S terminator (35S t) (Key et al. 1987. Science 236: 1299–1302 and Odell et al. 1985. Nature 313: 810–812) and this expression cassette was ligated into above mentioned vector. This resulted in the final plant transformation vector pVIC-galT, as shown schematically in FIG. 4.

4.2 Transformation of Potato Explants

Young leaves useful for the transformation of potato were prepared from leaves of 28 d old in vitro shoot cultures. The leaves were cut off avoiding the meristem at the leaf corner and were cut twice across the midvein. The explants were inoculated for 30 min. with a suspension of *Agrobacterium tumefaciens* strain EHA101 (OD$_{660}$=0.5) harbouring the transformation vector described above. After inoculation, the explants were dried carefully on filterpaper and left for co-cultivation for 3 d in dim light.

4.3. Selection of Transgenic Potato Shoots on Galactose Containing Media

After co-culture, the explants were transferred to selection medium consisting of MS-medium (Murashige and Skoog 1962. Physiol. Plant. 15: 473–497) supplemented with 500 mg/l carbenicillin and various concentrations of sucrose and galactose. After 3 and 6 weeks, shoots were harvested and transgenicity was evaluated by subjecting the harvested shoots to the assay for β-glucuronidase activity (Jefferson et al. 1987. Plant Mol. Biol. Rep. 5: 387–405), a marker enzyme encoded by a gene placed adjacent the selective gene on the T-DNA of the transformation vector (FIG. 4). The number of transgenic shoots isolated on the various selection media is indicated in the table below.

| Galactose concentration (g/l) | Sucrose concentration (g/l) | No. of transgenic shoots | Transformation frequency (%) |
|---|---|---|---|
| 0 | 20 | 0 | 0 |
| 1.25 | 10 | 3 | 6.0 |
| 1.25 | 15 | 7 | 14.0 |
| 1.25 | 20 | 3 | 6.0 |
| 2.5 | 10 | 1 | 2.0 |
| 2.5 | 15 | 0 | 0 |
| 2.5 | 20 | 4 | 8.0 |

The data show that it is possible to select transgenic shoots of a plant, transformed with a gene encoding an enzyme that enables or enhances the ability of the transformed shoots to reduce the toxicity of galactose.

In an other experiment, a few transgenic potato shoots (4%) were harvested on a medium devoid of galactose. Without wishing to be bound by theory we believe that this selective effect may be related to a stimulating effect of the inserted selective gene per se and/or the expression product thereof per se on the regeneration potential of the transgenic cells.

In combination with the toxicological sudies, the fact that transgenic potato shoots can be selected on galactose-containing media suggests that transgenic shoots of other plant species that are unable to grow on or inhibited by galactose also may be selected.

Without wishing to be bound by theory, we also believe that the degree of selectivity may differ due to the choice of the selection media—which may contain galactose and/or metabolic precursors and/or metabolic derivatives and/or derivatives of galactose, alone or in combination with other carbohydrate/energy source(s) such as sucrose, glucose, fructose, maltose which may or may not affect the effect of galactose. By way of example, it may be possible to yield similar or even substantially higher transformation frequencies.

Without wishing to be bound by theory, we also believe that the degree of selectivity may differ among different varieties/cultivars/subspecies of a plant species. Also, other physical and/or chemical and/or biological parameters affecting the effect of galactose may be expected to have an impact on the number of selectable transgenic shoots, possibly increasing the transformation frequencies significantly.

EXAMPLE 5

Transgenic Rape Seed

Hypocotyl explants of oil seed rape were prepared using a protocol modified according to Radke et al. (1988. Theor. Appl. Genet. 78: 161–168). Hypocotyls of 5 d old seedlings were cut into 1 cm segments and inoculated with a suspension of *Agrobacterium tumefaciens* strain EHA101 (OD$_{660}$= 0.1–0.5, prepared according to standard procedures). After inoculation, the explants were dried carefully on filterpaper before co-cultivation.

Selection of Transgenic Oil Seed Rape on Galactose Containing Media

After co-culture, the explants were transferred to selection medium consisting of modified MS-medium (Murashige and Skoog 1962. Physiol. Plant. 15: 473–497) supplemented with 500 mg/l carbenicillin and various concentrations of sucrose and galactose. After 7–8 weeks, shoots were harvested and transgenicity was evaluated by subjecting the harvested shoots to the assay for β-glucuronidase activity (Jefferson et al. 1987. Plant Mol. Biol. Rep. 5: 387–405), a marker enzyme encoded by a gene placed adjacent the selective gene on the T-DNA of the transformation vector (FIG. 3). The number of harvested shoots which were more than 50% β-glucuronidase-positive is indicated in the table below.

| Galactose concentration (g/l) | Sucrose concentration (g/l) | No. of transgenic shoots | Transformation frequency (%) |
|---|---|---|---|
| 0 | 20 | 0 | 0 |
| 2.5 | 10 | 4 | 1.0 |

The data show that it is possible to select transgenic shoots of oil seed rape, transformed with a gene encoding an enzyme that enables or enhances the ability of the transformed shoots to reduce the toxicity of galactose.

Without wishing to be bound by theory, we also believe that the degree of selectivity may differ due to the choice of the selection media—which may contain galactose and/or metabolic precursors and/or metabolic derivatives and/or derivatives of galactose, alone or in combination with other carbohydrate/energy source(s) such as sucrose, glucose, fructose, maltose which may or may not affect the effect of galactose. By way of example, it may be possible to yield similar or even substantially higher transformation frequencies.

Without wishing to be bound by theory, we also believe that the degree of selectivity may differ among different varieties/cultivars/subspecies of a plant species. Also, other physical and/or chemical and/or biological parameters affecting the effect of galactose may be expected to have an impact on the number of selectable transgenic shoots, possibly increasing the transformation frequencies significantly.

SUMMATION

In summation, therefore, the present invention relates to a selection method for selecting from a population of cells one or more selectable genetically transformed cells. The population of cells comprises selectable genetically transformed cells and possible non-transformed cells. Each of the selectable genetically transformed cells comprises a first expressable nucleotide sequence encoding a first expression product. Each of the selectable genetically transformed cells optionally comprises an optional second expressable nucleotide sequence encoding a second expression product and/or an optional third expressable nucleotide sequence encoding a third expression product. In the method a component is utilisable by the selectable genetically transformed cells by action of the first expressable nucleotide sequence or the first expression product and optionally by action of the optional second expressable nucleotide sequence or the optional second expression product and/or by action of the optional third expressable nucleotide sequence or the optional third expression product. The component can be present in an amount that is toxic to the non-transformed cells. The selection method comprises the step of introducing the population of cells to a medium, wherein the medium comprises the component and/or a derivative thereof and/or a precursor thereof and in an amount such that the component is or will be in an amount that is utilisable by the transformed cells but wherein the component is or will be in an amount that is toxic to the non-transformed cells. In the method, each of the first expression product and the optional second expression product and the optional third expression product is independently selected from an enzyme capable of metabolising galactose or a derivative thereof or a precursor thereof. In the method, the component and/or the derivative thereof and/or the precursor thereof is galactose or a derivative thereof or a precursor thereof.

The present invention also relates to a number of other aspects which also contain some or all of the same distinguishing technical features—such as: a composition comprising a population of cells comprising selectable genetically transformed cells and possible non-transformed cells, and a medium; a population of cells comprising selectable genetically transformed cells and possible non-transformed cells; a selectable genetically transformed cell; an organism comprising a selectable genetically transformed cell; a construct for genetically transforming a non-transformed cell to produce a selectable genetically transformed cell.

In one aspect of the present invention, the component is present in the medium.

Hence, this aspect of the present invention can be expressed as:

a selection method for selecting from a population of cells one or more selectable genetically transformed cells,
   wherein the population of cells comprises selectable genetically transformed cells and possible non-transformed cells;
      wherein each of the selectable genetically transformed cells comprises a first expressable nucleotide sequence encoding a first expression product;
   optionally wherein each of the selectable genetically transformed cells comprises an optional second expressable nucleotide sequence encoding a second expression product and/or an optional third expressable nucleotide sequence encoding a third expression product;
   wherein a component is utilisable by the selectable genetically transformed cells by action of the first expressable nucleotide sequence or the first expression product and optionally by action of the optional second expressable nucleotide sequence or the optional second expression product and/or by action of the optional third expressable nucleotide sequence or the optional third expression product;
   wherein the component can be present in an amount that is toxic to the non-transformed cells;
   the method comprising the step of introducing the population of cells to a medium, wherein the medium comprises the component and optionally a derivative thereof and/or a precursor thereof and in an amount such that the component is or will be in an amount that is utilisable by the transformed cells but wherein the component is or will be in an amount that is toxic to the non-transformed cells;

wherein each of the first expression product and the optional second expression product and the optional third expression product is independently selected from an enzyme capable of metabolising galactose or a derivative thereof or a precursor thereof; and wherein the component and/or the derivative thereof and/or the precursor thereof is galactose or a derivative thereof or a precursor thereof.

Likewise, this aspect of the present invention also relates to a number of other aspects which also contain some or all of the sane distinguishing technical features—such as: a composition comprising a population of cells comprising selectable genetically transformed cells and possible non-transformed cells, and a medium; a population of cells comprising selectable genetically transformed cells and possible non-transformed cells; a selectable genetically transformed cell; an organism comprising a selectable genetically transformed cell; a construct for genetically transforming a non-transformed cell to produce a selectable genetically transformed cell.

For some applications the component is detoxifiable by the selectable genetically transformed cells.

One aspect of this aspect of the present invention can be expressed as:

a selection method for selecting from a population of cells one or more selectable genetically transformed cells, wherein the population of cells comprises selectable genetically transformed cells and possible non-transformed cells;

wherein each of the selectable genetically transformed cells comprises a first expressable nucleotide sequence encoding a first expression product;

optionally wherein each of the selectable genetically transformed cells comprises an optional second expressable nucleotide sequence encoding a second expression product and/or an optional third expressable nucleotide sequence encoding a third expression product;

wherein a component or a derivative thereof or a precursor thereof when present in a detoxifiable amount in a medium is detoxifiable by the selectable genetically transformed cells by action of the first expressable nucleotide sequence or the first expression product and optionally by action of the optional second expressable nucleotide sequence or the optional second expression product and/or by action of the optional third expressable nucleotide sequence or the optional third expression product;

wherein the component or the derivative thereof or the precursor thereof can be present in an amount in a medium that is toxic to the non-transformed cells; the method comprising the step of introducing the population of cells to a medium, wherein the medium comprises the component and/or derivative thereof and/or the precursor therefor and in an amount that is detoxifiable by the transformed cells but in an amount that is toxic to the non-transformed cells;

wherein each of the first expression product and the optional second expression product and the optional third expression product is independently selected from an enzyme capable of metabolising galactose or a derivative thereof or a precursor thereof; and wherein the component and/or the derivative thereof and/or the precursor thereof is galactose or a derivative thereof or a precursor thereof.

Likewise, this aspect of the present invention also relates to a number of other aspects which also contain some or all of the same distinguishing technical features—such as: a composition comprising a population of cells comprising selectable genetically transformed cells and possible non-transformed cells, and a medium; a population of cells comprising selectable genetically transformed cells and possible non-transformed cells; a selectable genetically transformed cell; an organism comprising a selectable genetically transformed cell; a construct for genetically transforming a non-transformed cell to produce a selectable genetically transformed cell.

In one preferred aspect, the component is prepared in situ in the cells by processing a precursor therefor or a derivative thereof that was present in a medium in which the cells are or were present.

Hence, this preferred aspect can be expressed as:

a selection method for selecting from a population of cells one or more selectable genetically transformed cells, wherein the population of cells comprises selectable genetically transformed cells and possible non-transformed cells;

wherein each of the selectable genetically transformed cells comprises a first expressable nucleotide sequence encoding a first expression product;

optionally wherein each of the selectable genetically transformed cells comprises an optional second expressable nucleotide sequence encoding a second expression product and/or an optional third expressable nucleotide sequence encoding a third expression product;

wherein a component is utilisable by the selectable genetically transformed cells by action of the first expressable nucleotide sequence or the first expression product and optionally by action of the optional second expressable nucleotide sequence or the optional second expression product and/or by action of the optional third expressable nucleotide sequence or the optional third expression product;

wherein the component can be present in an amount that is toxic to the non-transformed cells;

the method comprising the step of introducing the population of cells to a medium, wherein the medium comprises a derivative of the component and/or a precursor of the component and in an amount such that the component is or will be in an amount that is utilisable by the transformed cells but wherein the component is or will be in an amount that is toxic to the non-transformed cells;

wherein each of the first expression product and the optional second expression product and the optional third expression product is independently selected from an enzyme capable of metabolising galactose or a derivative thereof or a precursor thereof; and wherein the component and/or the derivative thereof and/or the precursor thereof is galactose or a derivative thereof or a precursor thereof.

Likewise, this preferred aspect of the present invention also relates to a number of other aspects which also contain some or all of the same distinguishing technical features—such as: a composition comprising a population of cells comprising selectable genetically transformed cells and possible non-transformed cells, and a medium; a population of cells comprising selectable genetically transformed cells and possible non-transformed cells; a selectable genetically transformed cell; an organism comprising a selectable genetically transformed cell; a construct for genetically transforming a non-transformed cell to produce a selectable genetically transformed cell.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

REFERENCES

Bevan M, Flavell R B and Chilton M D. 1983. Nature 394, 184–187.
Bojsen K, Donaldson I, Haldrup A, Joersbo M, Kreiberg J D, Nielsen J, Okkels F T,
Petersen S G. 1994. Mannose and xylose based positive selection. WO94/20267.
Bowen B A. 1993. In 'Transgenic Plants' Vol. 1. Eds.: Kung S D and Wu R. Academic Press ISBN 0-12428781-6, pp. 89–146.
Chan P H and Hassid. 1975. Anal. Biochem. 64, 372–379.
Clermont S and Percheron F. 1979. Phytochem. 18, 1963–1965.
Dalessandro G and Northcote D H. 1977. Biochem J. 162, 281–288.
De Block M, Botterman J, Vandewiele M, Docky J, Toen C, Gossele V, Movva N R.
Thompson C, Van Montagu M and Leemans J. 1987. EMBO J. 6, 2513–2518.
Dressier K, Biedlingmaier S, Grossberger H, Kemmer J, Nolle U, Rodmanis-Blimer A and Hess, D. 1982. Z. Pflanzenphysiol. 107, 409–418.
Dey P M. 1983. Eur. J. Biochem. 136, 155–159.
Fan D-F and Feingold D S.1969. Plant Physiol. 44, 599–604.
Farkas G L. 1954. Biol. Zentralblatt 73, 506–521.
Flavell R B, Dart E, Fuchs R L and Fraley R T. 1992. Bio/Technology 10, 141–144.
Fraley R T, Rogers S G and Horsch R B. 1986. CRC Critical Reviews in Plant Science 4, 1–45.
Fraley R T, Rogers S G, Horsch R B, Sanders P, Flick J, Adams S, Bittner M, Brand L, Fink C, Fray J, Galluppi G, Goldberg S. and Woo S. 1983. Proc. Natl. Acad. Sci. USA 80, 4803–4806.
Haldrup A. 1996. Ph. D. Thesis, University of Copenhagen, Denmark.
Hille J, Verheggen F, Roelvink P. Franssen H, Kammen AV and Zabel P. 1986. Plant Mol. Biol. 7, 171–176.
Hughes R and Street H E. 1974. Ann. Bot. 38: 555–564.
Joersbo M. 1997. Antibiotic resistance genes and transgenic plants. Nordic Seminar,
Oslo, ISBN 82-91683-04-2 pp. 69–78.
Joersbo M and Okkels F r. 1996. Plant Cell Rep16, 219–221.
Joersbo M, Donaldson I, Pedersen SG, Brunstedt J and Okkels FT. 1998. Mol. Breeding, 4: 111–117.
Maretzki A and Thom M. 1978. Plant Physiol. 61, 544–548.
Neufeld E F, Feingold D S and Hassid W Z. 1960. J. Biol. Chem. 235, 906–909.
Okkels FT, Ward J L and Joersbo M. 1997. Phytochem. 46, 801–804.
Roberts R M, Heishamn A and Wicklin C. 1971. Plant Physiol. 48, 3642.
Shah D M, Horsch R B, Klee H J, Kishore G M, Winter J A, Turner N E, Hironaka C M,
Sanders P R, Gasser CS, Aykent S, Siegel N R, Rogers S G and Fraley R T. 1986. Science 233, 478–481.
Stalker D M, McBride K F and Malyj L D. 1988. Science 242, 419–423.
Streber W R and Willmitzer L. 1989. Bio/Technology 7, 811–816.
Waldron C, Murphy E B, Roberts J L, Gustafson, G D, Armour S L and Malcolm S K. 1985. Plant Mol. Biol. 5, 103–108.
Yoder J I and Goldsbrough P. 1994. Bio/Technol. 12, 263–267.

What is claimed is:

1. A process for selecting transformed plant cells or plant tissue comprising:
   a) transforming plant cells or plant tissue that are sensitive to galactose toxicity with one or more polynucleotide molecule encoding UDP-glucose dependent uridyl transferase;
   b) exposing the plant cells or tissue to galactose, wherein galactose is toxic to non-transformed plant cells or plant tissue; and
   c) selecting transformed plant cells or plant tissue that are insensitive to galactose toxicity.

2. The process of claim 1, additionally comprising transforming the plant cells or plant tissue with one or more polynucleotide encoding one or more of:
   i) UTP-dependent pyrophosphorylase;
   ii) galactokinase.

3. The process of claim 1, additionally comprising transforming the plant cells or plant tissue with one or more polynucleotide encoding:
   i) UTP-dependent pyrophosphoxylase; and
   ii) galactokinase.

4. The process of claim 1, additionally comprising transforming the plant cells or plant tissue with one or more polynucleotide encoding UTP-dependent pyrophosphorylase.

5. The process of claim 1, wherein said exposing comprises adding galactose to the plant cells or plant tissue in culture medium.

6. The process of claim 1, wherein said exposing comprises providing galactose-1-phosphate to the plant cells or plant tissue.

7. The process of claim 1, wherein said exposing comprises providing UDP-galactose to the plant cells or plant tissue.

8. The process of claim 1, wherein said plant cells or plant tissue are further exposed to a galactosidase that produces galactose from a galactose precursor.

9. The process of claim 1, wherein said plant cells or plant tissue are incubated in a culture medium containing one or more galactose precursor selected from the group consisting of lactose, melibiose, raffinose, stachyose, verbascose, galactinol, galactose pentaacetate, and galactose methyl galactoside; and
   wherein said medium further comprises an enzyme that converts said precursor to galactose.

10. The process of claim 1, wherein said plant cells or plant tissue are incubated in a culture medium containing one or more galactose derivative selected from the group consisting of galactose-1-phosphate and UDP-galactose.

11. The process of claim 1, wherein said plant cells or plant tissue are comprise tobacco, cotton, rape seed, potato, or maize plant cells or plant issue.

12. The process of claim 1, wherein said transforming further comprises transforming said plant cells or plant tissue with one or more heterologous nucleotide sequence of interest.

13. Transformed plant cells or plant tissue selected by the process of claim 1.

14. A transformed plant comprising plant cells or plant tissue selected by the process of claim 1.

15. A process for selecting transformed plant cells or plant tissue comprising:
   a) transforming plant cells in vitro or plant tissues in vitro that are sensitive to galactose toxicity with a polynucleotide encoding UDP-glucose-dependent uridyl transferase;
   b) exposing the plant cells or plant tissue to galactose, wherein said galactose is toxic to non transformed plant cells or plant tissue; and
   c) selecting transformed plant cells or plant tissue that are insensitive to galactose toxicity from a population of genetically nontransformed plant cells or plant tissue, wherein the galactose is toxic to the nontransformed plant cells.

16. A process for selecting transformed plant cells or plant tissue comprising:
   a) transforming plant cells or plant tissues that are sensitive to galactose toxicity with a transformation vector comprising a heterologous promoter operably linked to a polynucleotide molecule encoding UDP-glucose-dependent uridyl transferase;
   b) exposing the plant cells or plant tissue to galactose, wherein said galactose is toxic to non transformed plant cells or plant tissue; and
   c) selecting transformed plant cells or plant tissue that are insensitive to galactose toxicity from a population of genetically nontransformed plant cells or plant tissue, wherein the galactose is toxic to the nontransformed plant cells.

17. A process for selecting transformed plant cells or plant tissue comprising:
   a) transforming plant cells in vitro or plant tissues in vitro that are sensitive to galactose toxicity with a transformation vector comprising a heterologous promoter operably linked to a polynucleotide molecule encoding UDP-glucose-dependent uridyl transferase;
   b) exposing the plant cells or plant tissue to galactose, wherein said galactose is toxic to non transformed plant cells or plant tissue; and
   c) selecting transformed plant cells or plant tissue that are insensitive to galactose toxicity from a population of genetically nontransformed plant cells or plant tissue, wherein the galactose is toxic to the nontransformed plant cells.

* * * * *

UNITED STATES PATENT AND TRADEMARK OFFICE
CERTIFICATE OF CORRECTION

PATENT NO.        : 6,924,145 B1
APPLICATION NO. : 09/762629
DATED              : August 2, 2005
INVENTOR(S)       : Jorsboe et al.

It is certified that error appears in the above-identified patent and that said Letters Patent is hereby corrected as shown below:

Title page, [56] References Cited, Other Publications, Reference to Schumperli et al.: "257261" should read --257-261--

Title page, [56] References Cited, Other Publications, Reference to Daude et al.: "1-3" should read --1-7--

Title page, [56] References Cited, Other Publications, Reference to Maccratesi et al.: "Maccratesi" should read –Maceratesi-- and "Medine" should read --Medline--

Title page, [56] References Cited, Other Publications, Reference to Roberts et al.: "3645" should read --36-45--

Column 14
Line 14 "A minus symbol is missing above the "O" in the lowest symbol of "O"

Column 18
Line 1 "mannose" should read --manA--
Line 5 "mana" should read --manA--

Column 19
Line 55 "c-glucan" should read --α-glucan--

Column 20
Line 11, The following portion of the sentence has been omitted and should be inserted after the word "significantly": --increased. The two nucleotide sequences may be part of the same genetic construct and–

Column 26
Line 51 "PCT/EP96I03053" should read --PCT/EP96/03053--

Column 28
Line 26 "Maze" should read --Maize--

UNITED STATES PATENT AND TRADEMARK OFFICE
CERTIFICATE OF CORRECTION

PATENT NO. : 6,924,145 B1
APPLICATION NO. : 09/762629
DATED : August 2, 2005
INVENTOR(S) : Jorboe et al.

It is certified that error appears in the above-identified patent and that said Letters Patent is hereby corrected as shown below:

Column 32
Line 7 "34" should read --3-4--

Column 39
Line 38 "Dressier" should read --Dressler--

Column 43
Line 22 "or tissue" should read --or plant tissue--
Line 30 "pyrophosphorylase;" should read --pyrophosphorylase; and--
Line 34 "pyrophosphoxylase" should read --pyrophosphorylase--
Line 63 "tissue are comprise" should read --tissue comprise--

Signed and Sealed this

Nineteenth Day of September, 2006

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 1069
<212> TYPE: DNA
<213> ORGANISM: Escherichia coli

<400> SEQUENCE: 1
actgcaggaa cgaccatgac gcaatttaat cccgttgatc atccacatcg ccgctacaac      60
ccgctcaccg ggcaatggat tctggtttca ccgcaccgcg ctaagcgccc ctggcagggg     120
gcgcaggaaa cgccagccaa acaggtgtta cctgcgcacg atccagattg cttcctctgc     180
gcaggtaatg tgcgggtgac aggcgataaa aacccgatt acaccgggac ttacgttttc      240
actaatgact ttgcggcttt gatgtctgac acgccagatg cgccagaaag tcacgatccg     300
ctgatgcgtt gccagagcgc gcgcggcacc agccgggtga tctgcttttc accggatcac     360
agtaaaacgc tgccagagct cagcgttgca gcattgacgg aaatcgtcaa aacctggcag     420
gagcaaaccg cggaactggg gaaaacgtac ccatgggtgc aggtttttga aaacaaaggc     480
gcgccgatgg gctgctctaa cccgcatccg cacggtcaga tttgggcaaa tagcttcctg     540
```

-continued

```
cctaacgaag ctgagcgcga agaccgcctg caaaaagaat attttgccga acagaaatca    600
ccaatgctgg tggattatgt tcagcgcgag ctggcagacg tagccgtac  cgttgtcgaa    660 accgaacact ggttagccgt cgtgccttac tgggctgcct ggccgttcga aacgctactg    720
ctgcccaaag cccacgtttt acggatcacc gatttgaccg acgcccagcg cagcgatctg    780
gcgctggcgt tgaaaaagct gaccagtcgt tatgacaacc tcttccagtg ctccttcccc    840
tactctatgg gctggcacgg cgcgccattt aatggcgaag agaatcaaca ctggcagctg    900
cacgcgcact tttatccgcc tctgctgcgc tccgccaccg tacgtaaatt tatggttggt    960
tatgaaatgc tggcagagac ccagcgagac ctgaccgcga acaggcagc  agagcgtttg   1020 cgcgcagtca gcgatatcca ttttcgcgaa tccggagtgt aagtcgact             1069
```

<210> SEQ ID NO 2
<211> LENGTH: 348
<212> TYPE: PRT
<213> ORGANISM: Escherichia coli

<400> SEQUENCE: 2

```
Met Thr Gln Phe Asn Pro Val Asp His Pro His Arg Arg Tyr Asn Pro
 1               5                  10                  15

Leu Thr Gly Gln Trp Ile Leu Val Ser Pro His Arg Ala Lys Arg Pro
            20                  25                  30

Trp Gln Gly Ala Gln Glu Thr Pro Ala Lys Gln Val Leu Pro Ala His
        35                  40                  45

Asp Pro Asp Cys Phe Leu Cys Ala Gly Asn Val Arg Val Thr Gly Asp
    50                  55                  60

Lys Asn Pro Asp Tyr Thr Gly Thr Tyr Val Phe Thr Asn Asp Phe Ala
65                  70                  75                  80

Ala Leu Met Ser Asp Thr Pro Asp Ala Pro Glu Ser His Asp Pro Leu
                85                  90                  95

Met Arg Cys Gln Ser Ala Arg Gly Thr Ser Arg Val Ile Cys Phe Ser
            100                 105                 110

Pro Asp His Ser Lys Thr Leu Pro Glu Leu Ser Val Ala Ala Leu Thr
        115                 120                 125

Glu Ile Val Lys Thr Trp Gln Glu Gln Thr Ala Glu Leu Gly Lys Thr
    130                 135                 140

Tyr Pro Trp Val Gln Val Phe Glu Asn Lys Gly Ala Pro Met Gly Cys
145                 150                 155                 160

Ser Asn Pro His Pro His Gly Gln Ile Trp Ala Asn Ser Phe Leu Pro
                165                 170                 175

Asn Glu Ala Glu Arg Glu Asp Arg Leu Gln Lys Glu Tyr Phe Ala Glu
            180                 185                 190

Gln Lys Ser Pro Met Leu Val Asp Tyr Val Gln Arg Glu Leu Ala Asp
        195                 200                 205

Gly Ser Arg Thr Val Val Glu Thr Glu His Trp Leu Ala Val Val Pro
    210                 215                 220

Tyr Trp Ala Ala Trp Pro Phe Glu Thr Leu Leu Leu Pro Lys Ala His
225                 230                 235                 240

Val Leu Arg Ile Thr Asp Leu Thr Asp Ala Gln Arg Ser Asp Leu Ala
                245                 250                 255

Leu Ala Leu Lys Lys Leu Thr Ser Arg Tyr Asp Asn Leu Phe Gln Cys
            260                 265                 270

Ser Phe Pro Tyr Ser Met Gly Trp His Gly Ala Pro Phe Asn Gly Glu
        275                 280                 285
```

```
-continued

Glu Asn Gln His Trp Gln Leu His Ala His Phe Tyr Pro Pro Leu Leu
    290             295                 300

Arg Ser Ala Thr Val Arg Lys Phe Met Val Gly Tyr Glu Met Leu Ala
305                 310                 315                 320

Glu Thr Gln Arg Asp Leu Thr Ala Glu Gln Ala Ala Glu Arg Leu Arg
                325                 330                 335

Ala Val Ser Asp Ile His Phe Arg Glu Ser Gly Val
                340             345
```